US008093236B2

(12) United States Patent
Ogawa

(10) Patent No.: US 8,093,236 B2
(45) Date of Patent: Jan. 10, 2012

(54) WEEKLY ADMINISTRATION OF DIPEPTIDYL PEPTIDASE INHIBITORS

(75) Inventor: Atsushi Ogawa, Osaka (JP)

(73) Assignee: Takeda Pharmaceuticals Company Limited, Osaka (JP)

( * ) Notice: Subject to any disclaimer, the term of this patent is extended or adjusted under 35 U.S.C. 154(b) by 614 days.

(21) Appl. No.: 12/046,373

(22) Filed: Mar. 11, 2008

(65) Prior Publication Data
US 2008/0275072 A1 Nov. 6, 2008

Related U.S. Application Data

(60) Provisional application No. 60/894,624, filed on Mar. 13, 2007.

(51) Int. Cl.
A61K 31/00 (2006.01)
A61K 31/55 (2006.01)
A61K 31/505 (2006.01)
A61K 31/44 (2006.01)
A61K 31/425 (2006.01)

(52) U.S. Cl. .......... 514/210.2; 514/217.05; 514/217.06; 514/275; 514/342; 514/367

(58) Field of Classification Search .............. 514/210.2, 514/217.05, 217.06, 275, 342, 367
See application file for complete search history.

(56) References Cited

U.S. PATENT DOCUMENTS

| | | | |
|---|---|---|---|
| 3,322,756 A | 5/1967 | Hilmer et al. |
| 3,544,570 A | 12/1970 | Timmler et al. |
| 3,960,949 A | 6/1976 | Ahrens et al. |
| 4,494,978 A | 1/1985 | Chan |
| 4,687,777 A | 8/1987 | Meguro et al. |
| 4,935,493 A | 6/1990 | Bachovchin et al. |
| 5,002,953 A | 3/1991 | Hindley et al. |
| 3,823,135 A | 7/1994 | Pilgram et al. |
| 5,366,862 A | 11/1994 | Venton et al. |
| 5,387,512 A | 2/1995 | Balani et al. |
| 5,433,955 A | 7/1995 | Bredehorst et al. |
| 5,462,928 A | 10/1995 | Bachovchin et al. |
| 5,512,549 A | 4/1996 | Chen et al. |
| 5,543,396 A | 8/1996 | Powers et al. |
| 5,580,979 A | 12/1996 | Bachovchin |
| 5,601,986 A | 2/1997 | Takacs |
| 5,614,379 A | 3/1997 | MacKellar |
| 5,614,492 A | 3/1997 | Habener |
| 5,624,894 A | 4/1997 | Bodor |
| 5,798,344 A | 8/1998 | Kuroki et al. |
| 5,811,278 A | 9/1998 | Okamura et al. |
| 5,811,281 A | 9/1998 | Quaroni et al. |
| 5,814,460 A | 9/1998 | Venton et al. |
| 5,885,997 A | 3/1999 | Lohray et al. |
| 5,939,560 A | 8/1999 | Jenkins et al. |
| 5,965,532 A | 10/1999 | Bachovchin |
| 5,985,884 A | 11/1999 | Lohray et al. |
| 6,006,753 A | 12/1999 | Efendic |
| 6,011,155 A | 1/2000 | Villhauer |
| 6,090,786 A | 7/2000 | Augustyns et al. |
| 6,107,317 A | 8/2000 | Villhauer |
| 6,110,949 A | 8/2000 | Villhauer |
| 6,124,305 A | 9/2000 | Villhauer |
| 6,129,911 A | 10/2000 | Faris |
| 6,156,739 A | 12/2000 | Griffin et al. |
| 6,166,063 A | 12/2000 | Villhauer |
| 6,172,081 B1 | 1/2001 | Damon |
| 6,184,020 B1 | 2/2001 | Blinkovsky et al. |
| 6,201,132 B1 | 3/2001 | Jenkins et al. |
| 6,214,340 B1 | 4/2001 | Takeuchi et al. |
| 6,235,493 B1 | 5/2001 | Bissell et al. |
| 6,251,391 B1 | 6/2001 | Wilkinson et al. |
| 6,258,597 B1 | 7/2001 | Bachovchin |
| 6,261,794 B1 | 7/2001 | Chang |
| 6,265,551 B1 | 7/2001 | Duke-Cohan et al. |
| 6,303,661 B1 | 10/2001 | Demuth et al. |
| 6,309,868 B1 | 10/2001 | Monod |
| 6,310,069 B1 | 10/2001 | Lohray et al. |
| 6,319,893 B1 | 11/2001 | Demuth et al. |
| 6,325,989 B1 | 12/2001 | Duke-Cohan et al. |
| 6,335,429 B1 | 1/2002 | Cai et al. |
| 6,337,069 B1 | 1/2002 | Grouzmann et al. |
| 6,342,611 B1 | 1/2002 | Weber et al. |
| 6,355,614 B1 | 3/2002 | Wallner |
| 6,380,398 B2 | 4/2002 | Kanstrup et al. |
| 6,395,767 B2 | 5/2002 | Robl et al. |
| 6,432,969 B1 | 8/2002 | Villhauer |
| 6,447,772 B1 | 9/2002 | Houston |
| 6,448,045 B1 | 9/2002 | Levine et al. |
| 6,458,924 B2 | 10/2002 | Knudsen et al. |

(Continued)

FOREIGN PATENT DOCUMENTS

DE 21 50 686 A1 4/1973

(Continued)

OTHER PUBLICATIONS

Hcaplus 1995:104821, "Cyclodehydration of 4[(carboxymethyamino}pyridin-2-ones. A new, efficient synthesis of pyrrolo [3,2-c] pyridin-4-ones and pyrido [3,4-b] pyrrolizidin-1-ones" Edstrom et al. 1994.
Lambeir et al. "DPP4 from Bench to Bedside: An Update on Structural Properties, Functions, and Clinical Aspects of the Enzyme DPP4" Critical Reviews in Clinical Laboratories Sciences, 40(3):209-294 2003.
Pantani et al. "Bioisosterism: A Rational Approach in Drug Design", Chem. Rev. 1996, pp. 3147-3176.
Mukkerjee, Sucharita "[2+2] versus [4+2] cycloaddition reactions of 1,3-diaza-1,3-butadienes with various mono and disubtituted ketenes and supporting mechanistic considerations" Heter0cycles, vol. 47, No. 2, 1998 XP001539476.
Noguchi, Michihiko "Generation of NH-azomethine imine intermediates through the 1,2-hydrogen shift of hydrazones and their intermolecular cycloaddition reaction with olefinic dipolarophiles" Tetrahedron vol. 59 (2003), p. 4123-3.
Abdel-Fattah et al. Indian Journal of Heterocyclic Chemistry (1999), 8(3), 177-182. (Abstract, 2 pages).

(Continued)

Primary Examiner — Kevin E Weddington
(74) Attorney, Agent, or Firm — Mitchell R. Brustein

(57) ABSTRACT

Pharmaceutical compositions comprising 2-[6-(3-Amino-piperidin-1-yl)-3-methyl-2,4-dioxo-3,4-dihydro-2H-pyrimidin-1-ylmethyl]-4-fluoro-benzonitrile and pharmaceutically acceptable salts thereof are provided as well as kits and articles of manufacture comprising the pharmaceutical compositions as well as methods of using the pharmaceutical compositions.

12 Claims, 2 Drawing Sheets

U.S. PATENT DOCUMENTS

| | | |
|---|---|---|
| 6,485,955 B1 | 11/2002 | Huber et al. |
| 6,495,544 B2 | 12/2002 | Hasen, Jr. et al. |
| 6,500,804 B2 | 12/2002 | Demuth et al. |
| 6,518,277 B1 | 2/2003 | Sadhu et al. |
| 6,521,644 B1 | 2/2003 | Broqua |
| 6,528,486 B1 | 3/2003 | Larsen et al. |
| 6,545,170 B2 | 4/2003 | Pitzele et al. |
| 6,548,481 B1 | 4/2003 | Demuth et al. |
| 6,548,529 B1 | 4/2003 | Robl et al. |
| 6,555,519 B2 | 4/2003 | Washburn |
| 6,555,521 B2 | 4/2003 | Hermeling et al. |
| 6,559,188 B1 | 5/2003 | Gatlin et al. |
| 6,573,096 B1 | 6/2003 | Chen |
| 6,573,287 B2 | 6/2003 | Sulsky et al. |
| 6,586,198 B2 | 7/2003 | Brown |
| 6,608,038 B2 | 8/2003 | Caplan et al. |
| 6,617,340 B1 | 9/2003 | Villhauer |
| 6,620,821 B2 | 9/2003 | Robl |
| 6,620,910 B1 | 9/2003 | Calas et al. |
| 6,627,636 B2 | 9/2003 | Robl |
| 6,645,995 B2 | 11/2003 | Kanstrup et al. |
| 6,664,273 B2 | 12/2003 | Burnett et al. |
| 6,673,815 B2 | 1/2004 | Devasthale et al. |
| 6,673,829 B2 | 1/2004 | Dorwald et al. |
| 6,686,337 B2 | 2/2004 | Connor |
| 6,699,871 B2 | 3/2004 | Edmondson et al. |
| 6,703,238 B2 | 3/2004 | Bachovchin |
| 6,706,742 B2 | 3/2004 | De Nanteuil et al. |
| 6,710,040 B1 | 3/2004 | Hulin et al. |
| 6,716,843 B2 | 4/2004 | De Nanteuil et al. |
| 6,727,261 B2 | 4/2004 | Gobbi et al. |
| 6,727,271 B2 | 4/2004 | Cheng et al. |
| 6,747,035 B2 | 6/2004 | Guadilliere et al. |
| 6,800,650 B2 | 10/2004 | Boehringer et al. |
| 6,803,357 B1 | 10/2004 | Bachovchin et al. |
| 6,825,169 B1 | 11/2004 | Bachovchin et al. |
| 6,861,440 B2 | 3/2005 | Boehringer et al. |
| 6,867,205 B2 | 3/2005 | Boehringer et al. |
| 6,998,502 B1 | 2/2006 | Majeed et al. |
| 7,125,881 B2 | 10/2006 | Bailey et al. |
| 7,230,000 B1 | 6/2007 | Finer et al. |
| 7,304,086 B2 | 12/2007 | Schilling et al. |
| 7,371,871 B2 | 5/2008 | Schilling et al. |
| 7,470,700 B2 | 12/2008 | Feng et al. |
| 7,576,076 B2 | 8/2009 | Clark et al. |
| 2001/0018210 A1 | 8/2001 | Bachovchin et al. |
| 2001/0020006 A1 | 9/2001 | Demuth et al. |
| 2001/0031780 A1 | 10/2001 | Kanstrup et al. |
| 2001/0047078 A1 | 11/2001 | Chang |
| 2001/0051646 A1 | 12/2001 | Demuth et al. |
| 2002/0006899 A1 | 1/2002 | Pospisilik et al. |
| 2002/0016100 A1 | 2/2002 | Okabe et al. |
| 2002/0019411 A1 | 2/2002 | Robl et al. |
| 2002/0037829 A1 | 3/2002 | Aronson et al. |
| 2002/0041871 A1 | 4/2002 | Brudnak |
| 2002/0049153 A1 | 4/2002 | Bridon et al. |
| 2002/0049164 A1 | 4/2002 | Demuth et al. |
| 2002/0061839 A1 | 5/2002 | Scharpe et al. |
| 2002/0071838 A1 | 6/2002 | Demuth et al. |
| 2002/0077340 A1 | 6/2002 | Sulsky et al. |
| 2002/0082292 A1 | 6/2002 | Sahoo et al. |
| 2002/0082427 A1 | 6/2002 | Demuth et al. |
| 2002/0103242 A1 | 8/2002 | Sahoo et al. |
| 2002/0103384 A1 | 8/2002 | Kanstrup et al. |
| 2002/0110560 A1 | 8/2002 | Demuth et al. |
| 2002/0115843 A1 | 8/2002 | Oi et al. |
| 2002/0132979 A1 | 9/2002 | Chen |
| 2002/0147130 A1 | 10/2002 | Huber et al. |
| 2002/0147157 A1 | 10/2002 | Connor |
| 2002/0155565 A1 | 10/2002 | Garin-Chesa et al. |
| 2002/0164759 A1 | 11/2002 | Travis et al. |
| 2002/0165164 A1 | 11/2002 | Demuth et al. |
| 2002/0169159 A1 | 11/2002 | Medina et al. |
| 2002/0183367 A1 | 12/2002 | Sulsky et al. |
| 2002/0193390 A1 | 12/2002 | Villhauer |
| 2002/0198205 A1 | 12/2002 | Himmelsbach et al. |
| 2002/0198242 A1 | 12/2002 | Demuth et al. |
| 2002/0198380 A1 | 12/2002 | Belzer et al. |
| 2003/0008905 A1 | 1/2003 | Demuth et al. |
| 2003/0008925 A1 | 1/2003 | Demuth et al. |
| 2003/0027282 A1 | 2/2003 | Huber et al. |
| 2003/0040478 A1 | 2/2003 | Drucker et al. |
| 2003/0045464 A1 | 3/2003 | Hermeling et al. |
| 2003/0055052 A1 | 3/2003 | Peters et al. |
| 2003/0060412 A1 | 3/2003 | Prouty et al. |
| 2003/0060434 A1 | 3/2003 | Nielsen et al. |
| 2003/0069234 A1 | 4/2003 | Medina et al. |
| 2003/0087935 A1 | 5/2003 | Cheng et al. |
| 2003/0087950 A1 | 5/2003 | DeNanteuil et al. |
| 2003/0089935 A1 | 5/2003 | Fan et al. |
| 2003/0092630 A2 | 5/2003 | Demuth et al. |
| 2003/0092697 A1 | 5/2003 | Cheng et al. |
| 2003/0096846 A1 | 5/2003 | Cheng et al. |
| 2003/0096857 A1 | 5/2003 | Evans et al. |
| 2003/0100563 A1 | 5/2003 | Edmondson et al. |
| 2003/0103968 A1 | 6/2003 | Amelsberg et al. |
| 2003/0105077 A1 | 6/2003 | Kanstrup et al. |
| 2003/0119736 A1 | 6/2003 | Demuth et al. |
| 2003/0119738 A1 | 6/2003 | Niestroj et al. |
| 2003/0119750 A1 | 6/2003 | Demuth et al. |
| 2003/0125304 A1 | 7/2003 | Demuth et al. |
| 2003/0130199 A1 | 7/2003 | von Hoersten et al. |
| 2003/0130281 A1 | 7/2003 | Boehringer et al. |
| 2003/0130306 A1 | 7/2003 | Devasthale et al. |
| 2003/0134802 A1 | 7/2003 | Demuth et al. |
| 2003/0135023 A1 | 7/2003 | Demuth et al. |
| 2003/0139429 A1 | 7/2003 | Cohen et al. |
| 2003/0139434 A1 | 7/2003 | Balkan et al. |
| 2003/0144206 A1 | 7/2003 | Knudsen et al. |
| 2003/0148961 A1 | 8/2003 | Heiser et al. |
| 2003/0149071 A1 | 8/2003 | Gobbi et al. |
| 2003/0153509 A1 | 8/2003 | Bachovchin et al. |
| 2003/0162820 A1 | 8/2003 | Demuth et al. |
| 2003/0166578 A1 | 9/2003 | Arch et al. |
| 2003/0166662 A1 | 9/2003 | Fryburg et al. |
| 2003/0166690 A1 | 9/2003 | Ebdrup et al. |
| 2003/0171358 A1 | 9/2003 | Jeppesen et al. |
| 2003/0171411 A1 | 9/2003 | Kodra et al. |
| 2003/0176357 A1 | 9/2003 | Pospisilik et al. |
| 2003/0181497 A1 | 9/2003 | Chen et al. |
| 2003/0186963 A1 | 10/2003 | Dorwald et al. |
| 2003/0187254 A1 | 10/2003 | Perry et al. |
| 2003/0191112 A1 | 10/2003 | Dorwald et al. |
| 2003/0195188 A1 | 10/2003 | Boehringer et al. |
| 2003/0195190 A1 | 10/2003 | Peschke et al. |
| 2003/0199451 A1 | 10/2003 | Mogensen et al. |
| 2003/0199528 A1 | 10/2003 | Kanstrup et al. |
| 2003/0199563 A1 | 10/2003 | Robl et al. |
| 2003/0199672 A1 | 10/2003 | Knudsen et al. |
| 2003/0203946 A1 | 10/2003 | Behrens et al. |
| 2003/0216382 A1 | 11/2003 | Boehringer et al. |
| 2003/0216450 A1 | 11/2003 | Evans et al. |
| 2003/0220345 A1 | 11/2003 | Hamby et al. |
| 2003/0225102 A1 | 12/2003 | Sankaranarayanan |
| 2003/0232761 A1 | 12/2003 | Hinke et al. |
| 2003/0236272 A1 | 12/2003 | Carr |
| 2004/0002495 A1 | 1/2004 | Sher et al. |
| 2004/0002609 A1 | 1/2004 | Hulin |
| 2004/0006062 A1 | 1/2004 | Smallheer et al. |
| 2004/0009972 A1 | 1/2004 | Ding et al. |
| 2004/0009998 A1 | 1/2004 | Dhar et al. |
| 2004/0034014 A1 | 2/2004 | Kanstrup et al. |
| 2004/0053369 A1 | 3/2004 | Abbott et al. |
| 2004/0054171 A1 | 3/2004 | Jensen et al. |
| 2004/0058876 A1 | 3/2004 | Hoffmann et al. |
| 2004/0063935 A1 | 4/2004 | Yasuda |
| 2004/0072874 A1 | 4/2004 | Sato et al. |
| 2004/0072892 A1 | 4/2004 | Fukushima et al. |
| 2004/0077645 A1 | 4/2004 | Himmelsbach et al. |
| 2004/0082497 A1 | 4/2004 | Evans et al. |
| 2004/0082607 A1 | 4/2004 | Oi et al. |
| 2004/0087587 A1 | 5/2004 | Himmelsbach et al. |
| 2004/0092478 A1 | 5/2004 | Rothermel et al. |
| 2004/0097510 A1 | 5/2004 | Himmelsbach et al. |
| 2004/0106655 A1 | 6/2004 | Kitajima et al. |
| 2004/0106656 A1 | 6/2004 | Ashton et al. |
| 2004/0106802 A1 | 6/2004 | Sankaranarayanan |

| | | | | | |
|---|---|---|---|---|---|
| 2004/0110817 A1 | 6/2004 | Hulin | EP | 0702013 | 3/1996 |
| 2004/0116328 A1 | 6/2004 | Yoshikawa et al. | EP | 0748800 | 12/1996 |
| 2004/0132713 A1 | 7/2004 | Hulin et al. | EP | 900568 A2 | 3/1999 |
| 2004/0132732 A1 | 7/2004 | Han et al. | EP | 900568 A2 | 10/1999 |
| 2004/0138148 A1 | 7/2004 | Fushimi et al. | EP | 1136482 A1 | 9/2001 |
| 2004/0138214 A1 | 7/2004 | Himmelsbach et al. | EP | 1197799 A1 | 4/2002 |
| 2004/0138215 A1 | 7/2004 | Eckhardt et al. | EP | 1229024 | 8/2002 |
| 2004/0147434 A1 | 7/2004 | Ansorge et al. | EP | 1398032 | 3/2004 |
| 2004/0152192 A1 | 8/2004 | Bachovchin et al. | FR | 2.162.106 | 11/1972 |
| 2004/0152745 A1 | 8/2004 | Jackson et al. | GB | 699812 | 11/1950 |
| 2004/0166125 A1 | 8/2004 | Himmelsbach et al. | GB | 1377642 | 12/1971 |
| 2004/0167133 A1 | 8/2004 | Edmondson et al. | GB | 1441665 A | 7/1976 |
| 2004/0167191 A1 | 8/2004 | Demuth et al. | GB | 1464248 A | 2/1977 |
| 2004/0167341 A1 | 8/2004 | Haffner et al. | GB | 2143542 A | 2/1985 |
| 2004/0171104 A1 | 9/2004 | Blinkovsky et al. | GB | 2230527 A | 10/1990 |
| 2004/0171555 A1 | 9/2004 | Demuth et al. | JP | 53005180 A | 1/1978 |
| 2004/0171848 A1 | 9/2004 | Haffner et al. | JP | 9295977 | 11/1997 |
| 2004/0176406 A1 | 9/2004 | Gobbi et al. | JP | 2002/338466 | 11/2002 |
| 2004/0176428 A1 | 9/2004 | Edmondson et al. | JP | 2003/128551 | 5/2003 |
| 2004/0180925 A1 | 9/2004 | Matsuno et al. | JP | 2004/99600 A | 4/2004 |
| 2004/0186153 A1 | 9/2004 | Yasuda et al. | JP | 2004/123738 A | 4/2004 |
| 2004/0198786 A1 | 10/2004 | Gretzke et al. | WO | WO 89/10701 | 11/1989 |
| 2004/0209891 A1 | 10/2004 | Broqua et al. | WO | WO 91/11457 | 8/1991 |
| 2004/0229820 A1 | 11/2004 | Bachovchin et al. | WO | WO 91/12001 | 8/1991 |
| 2004/0229848 A1 | 11/2004 | Demuth et al. | WO | WO 93/21162 | 1/1993 |
| 2004/0236102 A1 | 11/2004 | Brockunier et al. | WO | WO 93/08259 A3 | 4/1993 |
| 2004/0242566 A1 | 12/2004 | Feng et al. | WO | WO 93/24634 | 12/1993 |
| 2004/0242568 A1 | 12/2004 | Feng et al. | WO | WO 94/03055 | 2/1994 |
| 2004/0242636 A1 | 12/2004 | Haffner et al. | WO | WO 95/15309 | 6/1995 |
| 2004/0242898 A1 | 12/2004 | Hulin et al. | WO | WO 95/29691 | 11/1995 |
| 2004/0254167 A1 | 12/2004 | Biftu et al. | WO | WO 95/35031 | 12/1995 |
| 2004/0254226 A1 | 12/2004 | Feng et al. | WO | WO 96/02667 | 2/1996 |
| 2004/0259843 A1 | 12/2004 | Madar et al. | WO | WO 96/32384 | 10/1996 |
| 2004/0259870 A1 | 12/2004 | Feng et al. | WO | WO 96/38550 | 12/1996 |
| 2004/0259883 A1 | 12/2004 | Sakashita et al. | WO | WO 97/40832 | 11/1997 |
| 2004/0259902 A1 | 12/2004 | Boehringer et al. | WO | WO 98/00439 A2 | 1/1998 |
| 2004/0259903 A1 | 12/2004 | Boehringer et al. | WO | WO 98/00439 A3 | 1/1998 |
| 2004/0259919 A1 | 12/2004 | Magnin et al. | WO | WO 98/18763 | 5/1998 |
| 2005/0004117 A1 | 1/2005 | Feng et al. | WO | WO 98/19998 | 5/1998 |
| 2005/0014732 A1 | 1/2005 | Gulve et al. | WO | WO 98/24780 | 6/1998 |
| 2005/0014946 A1 | 1/2005 | Demuth et al. | WO | WO 98/50046 | 11/1998 |
| 2005/0020574 A1 | 1/2005 | Hauel et al. | WO | WO 98/51803 | 11/1998 |
| 2005/0026921 A1 | 2/2005 | Eckhardt et al. | WO | WO 99/02705 | 1/1999 |
| 2005/0032804 A1 | 2/2005 | Cypes et al. | WO | WO 99/16864 | 4/1999 |
| 2005/0038020 A1 | 2/2005 | Hamann et al. | WO | WO 99/17799 | 4/1999 |
| 2005/0043292 A1 | 2/2005 | Parker et al. | WO | WO 99/18856 | 4/1999 |
| 2005/0043299 A1 | 2/2005 | Evans et al. | WO | WO 99/28474 | 6/1999 |
| 2005/0058635 A1 | 3/2005 | Demuth et al. | WO | WO 99/38501 A2 | 8/1999 |
| 2005/0065144 A1 | 3/2005 | Feng et al. | WO | WO 99/38501 A3 | 8/1999 |
| 2005/0065145 A1 | 3/2005 | Cao | WO | WO 99/46272 | 9/1999 |
| 2005/0065148 A1 | 3/2005 | Feng et al. | WO | WO 99/47152 | 9/1999 |
| 2005/0070530 A1 | 3/2005 | Feng et al. | WO | WO 99/50249 A2 | 10/1999 |
| 2005/0070531 A1 | 3/2005 | Feng et al. | WO | WO 99/50249 A3 | 10/1999 |
| 2005/0070535 A1 | 3/2005 | Feng et al. | WO | WO 99/52893 | 10/1999 |
| 2005/0070706 A1 | 3/2005 | Feng et al. | WO | WO 99-61431 | 12/1999 |
| 2005/0075330 A1 | 4/2005 | Feng et al. | WO | WO 99/62914 | 12/1999 |
| 2005/0261271 A1 | 11/2005 | Feng | WO | WO 99/67278 | 12/1999 |
| 2006/0135767 A1 | 6/2006 | Feng et al. | WO | WO 99/67279 | 12/1999 |
| 2007/0060528 A1 | 3/2007 | Christopher et al. | WO | WO 00/07617 | 2/2000 |
| 2007/0060530 A1 | 3/2007 | Christopher et al. | WO | WO 00/09666 A2 | 2/2000 |
| 2007/0066635 A1 | 3/2007 | Andres et al. | WO | WO 00/09666 A3 | 2/2000 |
| 2008/0003283 A1 | 1/2008 | Feng et al. | WO | WO 00/10549 | 3/2000 |
| 2008/0108807 A1 | 5/2008 | Feng et al. | WO | WO 00/15211 A2 | 3/2000 |
| 2008/0108808 A1 | 5/2008 | Feng et al. | WO | WO 00/15211 A3 | 3/2000 |
| | | | WO | WO 00/20416 | 4/2000 |
| FOREIGN PATENT DOCUMENTS | | | WO | WO 00/76986 A1 | 4/2000 |
| DE | 2361551 A1 | 6/1975 | WO | WO 00/34241 | 6/2000 |
| DE | 2500024 A1 | 7/1976 | WO | WO 00/40583 | 7/2000 |
| DE | 2801289 A1 | 5/1979 | WO | WO 00/43366 | 7/2000 |
| DE | 2801289 C2 | 5/1979 | WO | WO 00/47219 A2 | 8/2000 |
| DE | 10256264 A | 6/2004 | WO | WO 00/47219 A3 | 8/2000 |
| EP | 0378255 A2 | 7/1990 | WO | WO 00/53171 | 9/2000 |
| EP | 0 442 473 A | 8/1991 | WO | WO 00/56296 A2 | 9/2000 |
| EP | 0505893 | 9/1992 | WO | WO 00/56296 A3 | 9/2000 |
| EP | 0547442 A1 | 6/1993 | WO | WO 00/56297 | 9/2000 |
| EP | 0547514 | 6/1993 | WO | WO 00/57721 A2 | 10/2000 |
| EP | 0574846 | 12/1993 | WO | WO 00/57721 A3 | 10/2000 |
| EP | 0587377 A2 | 3/1994 | WO | WO 01/14318 A2 | 3/2001 |
| EP | 0657452 | 6/1995 | WO | WO 01/14318 A3 | 3/2001 |

| | | | | | | |
|---|---|---|---|---|---|---|
| WO | WO 01/16301 | 3/2001 | | WO | WO 03/011814 | 2/2003 |
| WO | WO 01/19866 | 3/2001 | | WO | WO 03/011892 A2 | 2/2003 |
| WO | WO 01/23364 A1 | 4/2001 | | WO | WO 03/011892 A3 | 2/2003 |
| WO | WO 01/34594 A1 | 5/2001 | | WO | WO 03/014318 A2 | 2/2003 |
| WO | WO 01/40180 A2 | 6/2001 | | WO | WO 03/014318 A3 | 2/2003 |
| WO | WO 01/40180 A3 | 6/2001 | | WO | WO 03/015775 | 2/2003 |
| WO | WO 01/52825 A2 | 7/2001 | | WO | WO 03/016335 A2 | 2/2003 |
| WO | WO 01/52825 A3 | 7/2001 | | WO | WO 03/016335 A3 | 2/2003 |
| WO | WO 01/55105 | 8/2001 | | WO | WO 03/017936 A2 | 3/2003 |
| WO | WO 01/56988 A1 | 8/2001 | | WO | WO 03/017936 A3 | 3/2003 |
| WO | WO 01/62266 A2 | 8/2001 | | WO | WO 03/022871 A2 | 3/2003 |
| WO | WO 01/62266 A3 | 8/2001 | | WO | WO 03/024942 | 3/2003 |
| WO | WO 0155119 | 8/2001 | | WO | WO 03/024965 A2 | 3/2003 |
| WO | WO 01/68603 A2 | 9/2001 | | WO | WO 03/024965 A3 | 3/2003 |
| WO | WO 01/68603 A3 | 9/2001 | | WO | WO 03/053330 A2 | 3/2003 |
| WO | WO 01/70729 A1 | 9/2001 | | WO | WO 03/053330 A3 | 3/2003 |
| WO | WO 01/72290 A2 | 10/2001 | | WO | WO 03/026652 A1 | 4/2003 |
| WO | WO 01/72290 A3 | 10/2001 | | WO | WO 03/027080 A1 | 4/2003 |
| WO | WO 01/74299 | 10/2001 | | WO | WO 03/030946 A1 | 4/2003 |
| WO | WO 01/79206 | 10/2001 | | WO | WO 03/033524 A2 | 4/2003 |
| WO | WO 01/81304 | 11/2001 | | WO | WO 03/033524 A3 | 4/2003 |
| WO | WO 01/81337 | 11/2001 | | WO | WO 03/033671 A2 | 4/2003 |
| WO | WO 01/89569 | 11/2001 | | WO | WO 03/035057 A1 | 5/2003 |
| WO | WO 01/94597 | 12/2001 | | WO | WO 03/035067 | 5/2003 |
| WO | WO 01/96295 A2 | 12/2001 | | WO | WO 03/035640 A1 | 5/2003 |
| WO | WO 01/97808 A1 | 12/2001 | | WO | WO 03/037327 | 5/2003 |
| WO | WO 02/02560 A2 | 1/2002 | | WO | WO 03/037888 A1 | 5/2003 |
| WO | WO 02/04610 | 1/2002 | | WO | WO 03/038123 | 5/2003 |
| WO | WO 02/08931 | 1/2002 | | WO | WO 03/040114 | 5/2003 |
| WO | WO 02/09716 A | 2/2002 | | WO | WO 03/040174 A2 | 5/2003 |
| WO | WO 02/14271 | 2/2002 | | WO | WO 03/040174 A3 | 5/2003 |
| WO | WO 02/20488 A2 | 3/2002 | | WO | WO 03/045228 A2 | 6/2003 |
| WO | WO 02/20804 | 3/2002 | | WO | WO 03/045228 A3 | 6/2003 |
| WO | WO 02/26703 | 4/2002 | | WO | WO 03/045977 A2 | 6/2003 |
| WO | WO 02/28742 | 4/2002 | | WO | WO 03/045977 A3 | 6/2003 |
| WO | WO 02/30890 | 4/2002 | | WO | WO 03/048081 A2 | 6/2003 |
| WO | WO 02/30891 A1 | 4/2002 | | WO | WO 03/048081 A3 | 6/2003 |
| WO | WO 02/30891 C1 | 4/2002 | | WO | WO 03/048158 A1 | 6/2003 |
| WO | WO 02/31134 | 4/2002 | | WO | WO 03/051848 A2 | 6/2003 |
| WO | WO 02/34242 A2 | 5/2002 | | WO | WO 03/051848 A3 | 6/2003 |
| WO | WO 02/34242 A3 | 5/2002 | | WO | WO 03/055881 | 7/2003 |
| WO | WO 02/34900 | 5/2002 | | WO | WO 03/057144 A2 | 7/2003 |
| WO | WO 02/38541 | 5/2002 | | WO | WO 03/057144 A3 | 7/2003 |
| WO | WO 02/38742 A2 | 5/2002 | | WO | WO 03/057200 A2 | 7/2003 |
| WO | WO 02/38742 A3 | 5/2002 | | WO | WO 03/057666 A2 | 7/2003 |
| WO | WO 02/051836 | 7/2002 | | WO | WO 03/057666 A3 | 7/2003 |
| WO | WO 02/053170 A2 | 7/2002 | | WO | WO 03/063903 A2 | 8/2003 |
| WO | WO 02/053170 A3 | 7/2002 | | WO | WO 03/065983 A2 | 8/2003 |
| WO | WO 02/059301 | 8/2002 | | WO | WO 03/065983 A3 | 8/2003 |
| WO | WO 02/059343 A2 | 8/2002 | | WO | WO 03/068748 | 8/2003 |
| WO | WO 02/059343 A3 | 8/2002 | | WO | WO 03/068757 A1 | 8/2003 |
| WO | WO 02/062764 | 8/2002 | | WO | WO 03/072197 | 9/2003 |
| WO | WO 02/066627 | 8/2002 | | WO | WO 03/072556 A1 | 9/2003 |
| WO | WO 02/068420 | 9/2002 | | WO | WO 03/074500 A2 | 9/2003 |
| WO | WO 02/076450 | 10/2002 | | WO | WO 03/074500 A3 | 9/2003 |
| WO | WO 02/083109 A1 | 10/2002 | | WO | WO 03/076393 | 9/2003 |
| WO | WO 02/083128 | 10/2002 | | WO | WO 03/076414 | 9/2003 |
| WO | WO 02/092127 | 11/2002 | | WO | WO 03/076418 A1 | 9/2003 |
| WO | WO 02/094178 A2 | 11/2002 | | WO | WO 03/077935 | 9/2003 |
| WO | WO 02/096357 A2 | 12/2002 | | WO | WO 03/080070 A2 | 10/2003 |
| WO | WO 02/096357 A3 | 12/2002 | | WO | WO 03/080070 A3 | 10/2003 |
| WO | WO 03/000180 A2 | 1/2003 | | WO | WO 03/080633 | 10/2003 |
| WO | WO 03/000180 A3 | 1/2003 | | WO | WO 03/082817 A2 | 10/2003 |
| WO | WO 03/000181 A2 | 1/2003 | | WO | WO 03/082817 A3 | 10/2003 |
| WO | WO 03/000250 A1 | 1/2003 | | WO | WO 03/082859 | 10/2003 |
| WO | WO 03/000250 A3 | 1/2003 | | WO | WO 03/082898 A2 | 10/2003 |
| WO | WO 03/002530 | 1/2003 | | WO | WO 03/082898 A3 | 10/2003 |
| WO | WO 03/002531 | 1/2003 | | WO | WO 03/084940 A1 | 10/2003 |
| WO | WO 03/002553 | 1/2003 | | WO | WO 03/084940 B1 | 10/2003 |
| WO | WO 03/002596 A2 | 1/2003 | | WO | WO 03/092605 A2 | 11/2003 |
| WO | WO 03/002596 A3 | 1/2003 | | WO | WO 03/092605 A3 | 11/2003 |
| WO | WO 03/004496 | 1/2003 | | WO | WO 03/099279 A1 | 12/2003 |
| WO | WO 03/004498 | 1/2003 | | WO | WO 03/099286 | 12/2003 |
| WO | WO 03/007888 A2 | 1/2003 | | WO | WO 03/099818 A1 | 12/2003 |
| WO | WO 03/010197 A2 | 2/2003 | | WO | WO 03/101449 A2 | 12/2003 |
| WO | WO 03/010197 A3 | 2/2003 | | WO | WO 03/101449 A3 | 12/2003 |
| WO | WO 03/010314 A2 | 2/2003 | | WO | WO 03/101958 A2 | 12/2003 |
| WO | WO 03/010314 A3 | 2/2003 | | WO | WO 03/101958 A3 | 12/2003 |
| WO | WO 03/011807 | 2/2003 | | WO | WO 03/104207 A2 | 12/2003 |

| | | |
|---|---|---|
| WO | WO 03/104207 A3 | 12/2003 |
| WO | WO 03/104208 | 12/2003 |
| WO | WO 03/104229 | 12/2003 |
| WO | WO 03/106416 A2 | 12/2003 |
| WO | WO 03/106416 A3 | 12/2003 |
| WO | WO 03/106456 A2 | 12/2003 |
| WO | WO 03/106456 A3 | 12/2003 |
| WO | WO 2004/002535 A1 | 1/2004 |
| WO | WO 2004/002535 C1 | 1/2004 |
| WO | WO 2004/002986 A2 | 1/2004 |
| WO | WO 2004/002986 A3 | 1/2004 |
| WO | WO 2004/004655 A2 | 1/2004 |
| WO | WO 2004/004655 A3 | 1/2004 |
| WO | WO 2004/004661 A2 | 1/2004 |
| WO | WO 2004/004661 A3 | 1/2004 |
| WO | WO 2004/004665 A2 | 1/2004 |
| WO | WO 2004/004665 A3 | 1/2004 |
| WO | WO 2004/007446 | 1/2004 |
| WO | WO 2004/007468 | 1/2004 |
| WO | WO 2004/011640 | 2/2004 |
| WO | WO 2004/014860 A2 | 2/2004 |
| WO | WO 2004/014860 A3 | 2/2004 |
| WO | WO 2004/017989 A1 | 3/2004 |
| WO | WO 2004/018467 A2 | 3/2004 |
| WO | WO 2004/018467 A3 | 3/2004 |
| WO | WO 2004/018468 A2 | 3/2004 |
| WO | WO 2004/018468 A3 | 3/2004 |
| WO | WO 2004/018469 | 3/2004 |
| WO | WO 2004/020407 | 3/2004 |
| WO | WO 2004/024184 | 3/2004 |
| WO | WO 2004/026822 A2 | 4/2004 |
| WO | WO 2004/026822 A3 | 4/2004 |
| WO | WO 2004/028524 | 4/2004 |
| WO | WO 2004/031175 A2 | 4/2004 |
| WO | WO 2004/031175 A3 | 4/2004 |
| WO | WO 2004/031374 A2 | 4/2004 |
| WO | WO 2004/031374 A3 | 4/2004 |
| WO | WO 2004/032836 A2 | 4/2004 |
| WO | WO 2004/032836 A3 | 4/2004 |
| WO | WO 2004/032861 A2 | 4/2004 |
| WO | WO 2004/032861 A3 | 4/2004 |
| WO | WO 2004/033455 A2 | 4/2004 |
| WO | WO 2004/033455 A3 | 4/2004 |
| WO | WO 2004/037169 A2 | 5/2004 |
| WO | WO 2004/037169 A3 | 5/2004 |
| WO | WO 2004/037176 A2 | 5/2004 |
| WO | WO 2004/037176 A3 | 5/2004 |
| WO | WO 2004/037181 A2 | 5/2004 |
| WO | WO 2004/037181 A3 | 5/2004 |
| WO | WO 2004/041795 | 5/2004 |
| WO | WO 2004/043940 | 5/2004 |
| WO | WO 2004/046106 | 6/2004 |
| WO | WO 2004/048352 A2 | 6/2004 |
| WO | WO 2004/048352 A3 | 6/2004 |
| WO | WO 2004/050022 A2 | 6/2004 |
| WO | WO 2004/050022 A3 | 6/2004 |
| WO | WO 2004/050022 B1 | 6/2004 |
| WO | WO 2004/050022 C1 | 6/2004 |
| WO | WO 2004/050656 | 6/2004 |
| WO | WO 2004/050658 | 6/2004 |
| WO | WO 2004/052850 A2 | 6/2004 |
| WO | WO 2004/052850 A3 | 6/2004 |
| WO | WO 2004/058266 | 7/2004 |
| WO | WO 2004/062613 A2 | 7/2004 |
| WO | WO 2004/064778 A2 | 8/2004 |
| WO | WO 2004/064778 A3 | 8/2004 |
| WO | WO 2004/067509 | 8/2004 |
| WO | WO 2004/069162 A2 | 8/2004 |
| WO | WO 2004/069162 A3 | 8/2004 |
| WO | WO 2004/071454 A2 | 8/2004 |
| WO | WO 2004/071454 A3 | 8/2004 |
| WO | WO 2004/075815 A2 | 9/2004 |
| WO | WO 2004/075815 A3 | 9/2004 |
| WO | WO 2004/075891 | 9/2004 |
| WO | WO 2004/076401 | 9/2004 |
| WO | WO 2004/076433 | 9/2004 |
| WO | WO 2004/076434 | 9/2004 |
| WO | WO 2004/078777 A2 | 9/2004 |
| WO | WO 2004/078777 A3 | 9/2004 |
| WO | WO 2004/080958 A2 | 9/2004 |
| WO | WO 2004/080958 A3 | 9/2004 |
| WO | WO 2004/082599 A2 | 9/2004 |
| WO | WO 2004/083212 | 9/2004 |
| WO | WO 2004/085408 A1 | 10/2004 |
| WO | WO 2004/085661 A2 | 10/2004 |
| WO | WO 2004/085661 A3 | 10/2004 |
| WO | WO 2004/087053 A3 | 10/2004 |
| WO | WO 2004/087053 C2 | 10/2004 |
| WO | WO 2004/087650 A2 | 10/2004 |
| WO | WO 2004/087650 A3 | 10/2004 |
| WO | WO 2004/087880 A2 | 10/2004 |
| WO | WO 2004/087880 A3 | 10/2004 |
| WO | WO 2004/087880 C1 | 10/2004 |
| WO | WO 2004/089362 | 10/2004 |
| WO | WO 2004/096806 | 11/2004 |
| WO | WO 2004/098625 | 11/2004 |
| WO | WO 2004/099134 | 11/2004 |
| WO | WO 2004/099185 | 11/2004 |
| WO | WO 2004/101514 | 11/2004 |
| WO | WO 2004/103276 A2 | 12/2004 |
| WO | WO 2004/103276 A3 | 12/2004 |
| WO | WO 2004/103993 | 12/2004 |
| WO | WO 2004/104215 | 12/2004 |
| WO | WO 2004/104216 | 12/2004 |
| WO | WO 2004/110436 | 12/2004 |
| WO | WO 2004/111041 | 12/2004 |
| WO | WO 2004/111051 | 12/2004 |
| WO | WO 2004/112701 A2 | 12/2004 |
| WO | WO 2004/112701 A3 | 12/2004 |
| WO | WO 2005/000846 | 1/2005 |
| WO | WO 2005/003135 | 1/2005 |
| WO | WO 2005/004906 A2 | 1/2005 |
| WO | WO 2005/011581 A2 | 2/2005 |
| WO | WO 2005/011581 A3 | 2/2005 |
| WO | WO 2005/012249 A2 | 2/2005 |
| WO | WO 2005/012249 A3 | 2/2005 |
| WO | WO 2005/016911 | 2/2005 |
| WO | WO 2005/019168 A2 | 3/2005 |
| WO | WO 2005/019168 A3 | 3/2005 |
| WO | WO 2005/095381 | 10/2005 |
| WO | WO 2007033265 | 3/2007 |
| WO | WO 2007033266 | 3/2007 |
| WO | WO 2007033350 | 3/2007 |

OTHER PUBLICATIONS

Abdel-Rahman, R. M.: Synthesis of some new fluorine bearing trisubstituted 3-thioxo-1, 2, 4-triazin-5-ones as potential anticancer agents: Farmaco, Edizione Scientifica, Societa Chimica Italiana, Pavia, IT, vol. 47, No. 3 (Mar. 1992), pp. 319-326, XP008000322.

Abstract of Lakhan et al. Journal of Indian Chemical Society (1987), 64 (5), 316-18 (2 pages).

Abstract of Shyam et al. Current Science (1975), 44(16), 572-4 (one page).

Abstract of Tiwari et al. Indian of Journal of Pharmaceutical Sciences (1978), 40(2), 40-3 (2 pages).

Adel Hamid et al. Scientia Pharmaceutica (2001), 69(4), 351-366.

Akahoshi, F. et al.: "Synthesis and pharmacological activitey of □riazole[1,5-a]triazine derivatives inhibiting eosinophilia." Journal of Medicinal Chemistry, vol. 41, No. 16, (Jul. 30, 1998), pp. 2985-2993, XP002390903.

Argaud, Doriane et al., Metaformin decreases gluconeogenesis by enhancing the pyruvate kinase flux in isolated rat hepatocytes, European J. Biochem. 213, 1341-1348 (1993).

Ashcroft, Stephen J.H. et al., Structure-activity relationships of alloxan-like compounds derived from uric acid, Br. J. Pharmac. (1986), 89 pp. 469-472.

Baker, B.R. et al., Irreversible Enzyme Inhibitors. On the Mode of Pyrimidine Binding of 5-alkyl and 5-Arylpyrimidines to Dihydrofolic Reductase (1,2), Journal of Heterocyclic Chemistry vol. 4 (1967) pp. 39-48.

Bal, Gunther, Dipeptidyl Peptidase IV and Prolyl Oligopeptidase: Design, Synthesis and Evaluation of Substrates and Inhibitors, (2002) Universiteit Antwerpen.

Banker, G.S. et al, "Modern Pharmaceutices, 3rd edition", Marcel Dekker, New York, 1996, pp. 451 and 596.

Barakat, S.E.S., Synthesis and hypoglycemic activity of some new 3-[4- [[[(cyclohexylamino) carbonyl] amino]sulfonyl]phenyl]-4(3H)-quinazolinones, Az. J. Pharm. Sci., vol. 25, (2000), pp. 48-57.

Barakat, S.E.S., Synthesis and Hypoglycemic Activity of Some New 4(3H)—Quinazolinone Analogues, Saudi Pharmaceutical Journal, vol. 8, No. 4 (2000) pp. 198-204.

Barnela et al. Indian Journal of Chemistry Section B: Organic Chemistry Including Medicinal Chemistry (1986), 25B(7), 709-11. (Abstract 2 pages).

Belgodere, Elena et al., Synthesis of Substituted Pyrimidines, Study of the Structure and of the Tautomeric Equilibria, (1976) Chem. Abstracts, Columbus, OH vol. 85 No. 9.

Bezuglyi, P.O. et al., Synthesis of arylsulfonyl hydrazide of 3-R-quinazolone-4-carbonyl-2-acid, Pharmaceutical Journal (1979), pp. 70-71.

Bhaduri, A.P. et al., Urinary Metabolite of 2-Piperazino-3 (H)-4-Quinazolone (Centpiperalone), A Potent Blood Sugar Lowering Agent, Indian J. Biochem. Biophys., vol. 12 (1975), pp. 413-414.

Borrell, J. I. et al.: "Synthesis, structure and cytotoxicity evaluation of palladium(II) complexes of 4-amino-3-hydrazino-1,2,4-triazin-5(4h)-on es and 4-amino-3-(n-methylhydrazino)-1,2,4-triazi N-5(4H)-ones" Anales De Quimica, vol. 91, No. 3/4, 1995, pp. 243-252, XP008000323.

Botta, M., Saladino, R., Lamba, D. Nicoletti, R.: Researches on Antiviral Agents. 31. Synthesis and Transformations of Racemic and Chiral 6-Oxiranyl Pyrimidinones, Tetrahedron, vol. 49, 1993, pp. 6053-6070, XP002329846.

Bouras, Mohammed, et al., Metabolism of enterostatin in rat intestine, brain, membranes and serum: differential involvement of proline-specific peptidases, Peptides, vol. 16, No. 3, (1995), pp. 399-405.

Brun, Jean-Frederic, et al., Effects of Oral Zinc Gluconate on Glucose Effectiveness and Insulin Sensitivity in Humans, Biological Trace Element Reserarch vol. 47 (1995), pp. 385-391.

Buckley, Di, Analysis of the Degradation of Insulinotropin [GLP-1 (7-37)] in Human Plasma and Production of Degradation Resistant Analogs.

Buysens, K. J. et al.: "Synthesis of New Pyrrolo[3,4-b]- and [3,4-c]□uinazol(on)es and related 1,7-Naphthyridinones and 2,7-naphthyridines via intramolecular diels-alder reactions of 2(1H)-pyrazinones" Tetrahedron, Elsevier Science Publishers, Amsterdam, NL, vol. 52, No. 27, (Jul. 1, 1996), pp. 9161-9178, XP004104003.

Caira M R: "Crystalline Polymorphism of Organic Compounds" Topics in Current Chemistry, Springer, Berlin, DE, vol. 198, 1998, pp. 163-208, XP001156954 ISSN: 0340-1022 p. 165.

Cecil Textbook of Medicine, edited by Bennet, J.C., and Plum F., 20th edition, vol. 1, 1004-10, 1996.

Chatterjee, A.K. et al., Effect of Centpiperalone in Insulin Deficient Diabetes, Indian Journal of Experimental Biology vol. 18 (1980), pp. 1005-1008.

Chatterjee, A.K. et al., Effect of Centpiperalone, a New Hypoglycemic Agent on Insulin Biosynthesis & Release from Isolated Pancreatic Islets of Rat, Indian Journal of Experimental Biology vol. 20 (1981) pp. 270-272.

Chenard et al. J. Med Chem. 2001, 44, 1710-1717.

Coppola, Gary M. et al., 1-Aminomethylisoquinoline-4-carboxylates as Novel Dipeptidylpeptidase IV Inhibitors, Bioorganic & Medicinal Chemistry Letters vol. 10 (2000), pp. 1555-1558.

Deacon, Carolyn F. et al., Both Subcutaneously and Intravenously Administered Glucagon-Like Peptide I are Rapidly Degraded From the $NH_2$-Terminus in Type II Diabetic Patients and in Healthy Subjects, Diabetes, vol. 44 (1996), pp. 1125-1131.

Deacon, Carolyn F. et al., Degradation of Glucagon-Like Peptide 1 in Vitro Yields an N-Terminally Truncated Peptide That is a Major Endogenous Metabolite in Vivo, Journal of Clinical Endocrinology and Metabolism vol. 80, No. 3 (1995), pp. 952-957.

Deacon, Carolyn F. et al., Dipeptidyl peptidase IV Inhibition as an Approach to the Treatment and Prevention of Type 2 Diabetes: a Historical Perspective, Biochemical and Biophysical Research Communications 294 (2002), pp. 1-4.

Deacon, Carolyn F. et al., Dipeptidyl peptidase IV Inhibition Influences GLP-1 Metabolism in Vivo, Regulatory Peptides vol. 64 Issues 1-3 (1996) p. 30.

Deacon, Carolyn F. et al., Dipeptidyl peptidase IV Inhibition Potentiates the Insulinotropic Effect of Glucagon-Like Peptide 1 in the Anesthetized Pig, Diabetes, vol. 47 (1998), pp. 764-769.

Demuth, Hans-Ulrich et al., Rebuttal to Deacon and Hoist: "Metaformin effects on □uinazolin peptidase IV degradation of glucagons-like peptide-1" versus "dipeptidyl peptidase inhibition as an approach to the treatment and prevention of type 2 diabetes: a historical perspective" Biochemical and Biophysical Research Communications 296 (2002) pp. 229-232.

Dey, Paramita D., et al., Regioselective [4+2] Cycloaddition versus Nucleophilic Reactions of N-Arylamino Substituted 1,3-Diaza-1,3-Butadienes with Ketenes: Synthesis of Pyrimidinone and Fused Pyrimidione Derivatives. Part II. Tetrahedron, vol. 53, No. 40, pp. 13829-13840, 1997.

Dumas, Donald J. "Total synthesis of peramine" Journal of Organic Chemistry, American Chemical Society, Easton, US, vol. 5, 1988, pp. 4650-4653, XP002087391.

Engel, Michael et al., The crystal structure of dipeptidyl peptidase IV (CD26) reveals its functional regulation and enzymatic mechanism, Proc. Nat. Acad. Sci. Early Edition (2003), pp. 1-6.

Fraisse, L., et al. Long-Chained Substituted Uric Acid and 5,6-Diaminouracil Derivatives as Novel Agents against Free Radical Processes: Synthesis and in Vitro Activity, Journal of Medicinal Chemistry, vol. 36, 1993, pp. 1456-1473, XP002329847.

Fraser & Kermack "The Reaction of Paludrine (Proguanil) with Ethyl Acetoacetate" 1951 pp. 2682-2686.

Garratt, Peter J. et al., A Novel Synthesis of Dihydropyrimidines, J. Chem. Soc., Chem. Commun. (1987), pp. 568-569.

Garratt, Peter J. et al., One-Carbon Compounds as Synthetic Intermediates. The Synthesis of Hydropyrimidines and Hydroquinazolines by Sequential Nucleophilic Addition to Diphenyl Cyanocarbonimidate With Concomitant Cyclization, J. Org. Chem. (1988), pp. 1062-1069.

Gazit, Aviv et al., Tyrphostins IV—Highly Potent Inhibitors of EGF Receptor Kinase. Structure-Activity Relationship Study of 4-Anilidoquinazolines, Bioorganic & Medicinal Chemistry, vol. 4, No. 8 (1996) pp. 1203-1207.

Green et al., Expert Opin. Emergin Drugs, 11(3); 525-539, 2006.

Guerrieri, N., et al., Vanadium Inhibition of Serine and Cysteine Proteases, Comparative Biochemistry and Physiology Part A 122 (1997), pp. 331-336.

Gupta, A. et al.: "Fluorine containing Biologically Active Agents: Synthesis of some new Pyrimidine Derivatives" J.Ind. Chem.Soc., vol. 71 1994, pp. 635-636, XP000889664 compound 1.

Gupta, C.M. et al., A Novel Class of Hypoglycaemic Agents: Syntheses & SAR in 2-Substituted 4(3H)-Quinazolones, 2-Substituted 4-Hydroxypolymethylene 5,6]pyrimidines & 3-Substituted 4-Oxopyrido [I,2-a] pyrimidines, Indian Journal of Chemistry, vol. 9 (1971), pp. 201-206.

Gupta, C.M. et al., Drugs Acting on the Central Nervous System. Syntheses of Substituted Quinazolones and Quinazolines and Triazepino-and Triazocionquinazolones, Division of Medicinal Chemistry, Central Drug Research Institute, Lucknow, India (1967), pp. 392-395.

Gupta, C.M. et al., New Potent Blood Sugar Lowering Compound, Nature, vol. 223 (1969), p. 524.

Hcaplus 121: 35089 Snider, Barry B. et al. Tetrahedron Ltrs 1994 35(4) 531-4.

Hcaplus 122: 132810 Snider, Barry B. et al. Jornal of Organic Chem. 1994, 59(26) 8065-70.

Hermecz, Istvan et al., Pyrido[1,2-a]Pyrimidines; New Chemical Entities in Medicinal Chemistry, Medicinal Research Reviews, vol. 8, No. 2 (1988) pp. 203-230.

Hinke, Simon A. et al., Metaformin Effects on Dipeptidylpeptidase IV Degradation of Glucagon-like Peptide-1, Biochemical and Biophysical Research Communications, 291 (2002) pp. 1302-1308.

Hinke, Simon A. et al., On Combination Therapy of Diabetes With Metaformin and Dipeptidyl Peptidase IV Inhibitors, Diabetes Care, vol. 25, No. 8 (2002) pp. 1490-1492.

Holz, George G. et al, Pancreatic Beta-Cells are Rendered Glucose-Competent by the Insulinotropic Hormone Glucagon-Like Peptide-1(7-37), Nature, vol. 361 (1993), pp. 362-365.

Jakubkiene, Virginija, et al., (G-Methyl-2methylsulfanyl-4-oxo-3,4-dihydro-3-pyrimidinyl)acetic acid and related compounds exhibiting anti-inflammatory activity. Pharmazie 57 (2002) 9, pp. 610-613.

Jones, Terence R., et al., Azafluorenes Containing Two Bridgehead Nitrogen Atoms. Journal of the Chemical Society, Perkin Transactions 1, No. 12, Dec. 1987, pp. 2585-2592.

Kesarwani, A. P. et al.: Solid-phase synthesis of ☐uinazoline-(3H)-ones with three-point diversity, Tetrahedron Letters, vol. 43, (2002) pp. 5579-5581.

Khalid, Noraini M., et al., Purification and Partial Characterization of a Prolyl-Dipeptidyl Aminopeptidase From *Lactobacillus helveticus* CNRZ 32, Applied and Environmental Microbiology (1990), pp. 381-388.

Kieffer, Timothy J. et al., Degradation of Glucose-Dependant Insulinotropic Polypeptide and Truncated Glucagon-Like Peptide 1 in Vitro and in Vivo by Dipeptidyl Peptidase IV, Endocrinology, vol. 136, No. 8 (1995) 3585-3596.

Kim, H.O. et al., Structure-Activity Relationships of 1,3-Dialkylxanthine Derivatives at Rat $A_3$ Adenosine Receptors, Journal of Medicinal Chemistry, vol. 37, 1994, pp. 3373-3382, XP002329848.

Kimura, Toshikiro et al., Oral Administration of Insulin as Poly(Vinyl Alcohol)-Gel Spheres in Diabetic Rats, Biological & Pharmaceutical Bulletin, vol. 19, No. 6 (1996), 897-900.

Kobe, J. et al.: "The synthesis of s-triazolo[4.3-a]1,3,5-triazines" Tetrahedron, Elsevier Science Publishers, Amsterdam, NL, vol. 26, Jul. 1970, pp. 3357-3368, XP002390908.

Koreeda, Yuji et al., Isolation and Characterization of Dipeptidyl Peptidase IV From *Prevotella loescheii* ATCC 15930, Archives of Oral Biology, 46 (2001), 759-766.

Kotra, L. P. et al.: "4-Azido-2-pyrimidone Nucleosides and Related Chemistry" Journal of Organic Chemistry, American Chemical Society. Easton, US, vol. 62, 1997, pp. 7267-7271, XP002390905.

Kozhevnikov et al. Tr. Perm. Sei.-Khoz. Inst. (1971), No. 79, 66-72 From ref. Zh., Khim. 1972, Abstr. No. 9Zh404 Journal (English Abstract attached).

Kusar, Mihael et al., Diethyl N,N-Dimethylaminomethylenemalonate in the Synthesis of Fused Heterocyclic Systems, Heterocyclic Chem. 33 (1996) pp. 1041-1046.

Li Jinping, et al., Permolybdate and Pertungstate—Potent Stimulators of Insulin Effects in Rat Adipocytes: Mechanism of Action, Biochemistry, 34 (1995) 6218-6225.

Lin, Jian, Total Synthesis and Biological Evaluation of Fluoroolefin-containing Dipeptidyl Isosteres as Inhibitors of Dipeptidyl Peptidase IV (CD26), Dissertation presented to State University of New York at Albany, Department of Chemistry (1998).

Loeser, Eric et al., Selective N-Alkylation of Primary Amines with Chloroacetamides Under pH-Controlled Aqueous Conditions, Synthetic Communications, 32(3) (2002) pp. 403-409.

Majim R. Berichet der Deutschen Chemischen Gesellschaft 1908 41 pp. 176-186.

Mall et al. Reactivity Difference of Cis-Trans Pairs: I Behavior of Stillbene Oxides and Activates Stibene Imines, 1987, Journal of Organic Chemistry, 1987, vol. 52, pp. 4812-4814.

Mannucci, Eduardo, et al., Effect of Metaformin on Glucagon-Like Peptide-1 (GLP-1) and Leptin Levels in Obese Nondiabetic Subjects, Diabetes Care, vol. 24, No. 3 (2001) 489-494.

Marcus et al. PubMed Abstract (Intervirology, 45/4-6):260-6) 2002.

Mentlein, Rolf et al., Dipeptidyl-Peptidase IV Hydrolyses gastric Inhibitory Polypeptide, Glucagon-Like Peptide-1(7-36)amide, Peptide Histidine Methionine and is Respoinsible for Their Degradation in Human Serum, Eur. J. Biochem, vol. 214, 829-835 (1993).

Molina, P. et al.: "Iminophosphorane-mediated annulation of 1,3,5-triazine to benzimidazole: Synthesis of 1,3,5-triazino[1,2-a]benzimidazoles" Synthesis 1992 Germany, No. 3, 1992- pp. 297-302, XP002390907.

Mukerjee, S.S. et al., Chronic Toxicity Studies of a Hypoglycemic Compound: Centpiperalone in Rats & Rhesus Monkeys, Indian Journal of Experimental Biology, vol. 17 (1979) pp. 1346-1349.

Mukerjee, S.S. et al., Effect of 2-piperazino-4(3H)-quinazolinone monoacetate on the tissue respiration, glucose uptake and lactic acid production by rat hemidiaphragm, Biochemical Pharmacology, vol. 23 (1974) 3066-3067.

Mukerjee, S.S. et al., Studies on the Mechanism of Centpiperalone-Induced Hypoglycemia, Acta Diabet. Lat 13, 8 (1976) p. 8.

Mukerjee, S.S. et al., Tissue Distribution of [$^3$H]Centpiperalone after Oral Administration, Indian J. Biochem. Biophys., vol. 17 (1980) pp. 399-401.

Mukherjee, Surath K. et al., A novel hypoglycemic compound, Biochemical Pharmacology, vol. 22 (1972) pp. 1529-1531.

Mukherjee, Surath K. et al., Effect of 2-piperazino-4(3H)-quinazolinone monoacetate on some aspects of carbohydrate metabolism of albino rats, Biochemical Pharmacology, vol. 22 (1973) pp. 2205-2206.

Mukherjee, Surath K. et al., Influence of Timing Oral Dosing of a Novel Hypoglycaemic Agent A-4166 in Relation to Food, Diabetologia vol. 38 A194 Supplement 1 (1995).

Mukherjee, Surath K. et al., Studies on the Metabolic Changes Induced by a Synthetic Insulinogenic Agent, Ind. J. Physiol. & Allied Sci., vol. 30, No. 3 (1976) pp. 105-116.

Murthy, G. Rama et al., New Hypoglycemic Agents: Part V—Synthesis & Hypoglycemic Activity of Some New 1-[[p-(4-OXO-2-Methyl/Phenyl-3 (4H)-Quinazolinyl) Phenyl]] 3-Aryl-2-Ureas, Indian Drugs, 25 (1) (1987) pp. 19-22.

Murthy, G. Rama et al., New Hypoglycemic Agents: Synthesis and Hypogylcemic Activity of Some New 1-[{p-(4-OXO-2-Substituted-3(4H)-Quinazolinyl)-Phenyl} Sulphonyl]-3-Aryl/Cyclohexyl-2-Thioureas, Current Science, vol. 56, No. 24 (1987) pp. 1263-1265.

Nakamura, Seiji et al., Effect of Chronic Vanadate Administration in Partially Depancreatized Rats, Diabetes Research and Clinical Practice 27 (1995) pp. 51-59. (Abstract Only).

Ohkubo, I., et al., Dipeptidyl Peptidase IV From Porcine Seminal Plasma: Purification, Characterization, and N-Terminal Amino Acid Sequence, J. Biochem. (Tokyo) (1994) 116(5) pp. 1182-11826.

Pandeya, S.N. et al., Synthesis of Some New Amidine Derivatives As Potent Hypoglycemic Agents, Pharmacological Research Communications, vol. 17, No. 8 (1985) pp. 699-709.

Pattanaik et al. Indian Journal of Chemistry, Section B; Organic Chemistry including Medicinal Chemistry (1998), 37B (12), 1304-1306 from STN CAS online search printout (3 pages).

Patent Abstracts of Japan, vol. 2003, No. 12, Xanthine Derivative, Dec. 5, 2003 & JP 2003 300977 A (Sumitomo Pharmaceut Co Ltd), Oct. 21, 2003, Abstract.

Patent Asbstracts of Japan Publication No. 2002338551, Publication Date Nov. 27, 2002.

Pauly, R.P. et al., Inhibition of Dipeptydyl Peptidase IV (DPIV) in Rat Results in Improved Glucose Tolerance, Regulatory Peptides vol. 64, Issues 1-3 (1996) p. 148.

Ram, Vishnu Ji et al., Synthesis and Antihyperglycemic Activity of Suitably Functionalized 3H-quinazolin-4-ones, Bioorganic & Medicinal Chemistry 11 (2003), pp. 2439-2444.

Rauchman, B.S. et al. "2,4—Diamino-5-benylpyrimidines and Analogues as antibacterial Agents", Journal of Med. Chem., vol. 23, 1980, pp. 384-391, XP002335048 Scheme II.

Sammour et al. Egyptian Journal of Chemistry (1979) Volume Date 1976, 19(6), 1109-16. (Abstract 2 pages).

Sawyer, James H. et al., Pyrido[1,2-a]pyrimidinium Salts. Part 1. Synthesis from 2-Aminopyridines and Interconversion with 2-(2-Acylvinylamino) pyridines, J.C.S. Perkin I (1972), 1138-1143.

Saxena, A.M. et al., Mode of action of three structurally different hypoglycemic agents: A comparative study, Indian Journal of Experimental Biology, vol. 34 (1996), pp. 351-355.

Sedo, Aleksi et al., Dipeptidyl peptidase IV-like molecules: homologous proteins or homologous activities? Biochimica et Biophysica Acta 1550 (2001), pp. 107-116.

Sekiya, T. et al., Pyrimidine derivatives. III (1) Synthesis of hypoglycemic 4-alkoxy-2-piperazino-activity of 6-polymethylenepyrmidines, Eur. J. Med. Chem. (1982), 75-79.

Senten, Kristel et al., Development of Potent and Selective Dipeptidyl Peptidase II Inhibitors, Bioorganic & Medicinal Chemistry Letters 12 (2002) pp. 2825-2828.

Seth, M. et al., Syntheses of 2-Substituted & 2,3-Distributed 4(3H)-Quinazolones, Indian Journal of Chemistry, vol. 14B (1975), 536-540.

Sharma, Arun K., et al. Tandem sigmatropic shifts in [4+2] cycloaddition reactions of 1,3-diazabuta-1,3-dienes with butadienylketene: synthesis of pyrimidinone derivatives. J. Chem. Soc., Perkin Trans. 1, 2002, 774-784.

Shimazawa, Rumiko et al., Novel Small Molecule Nonpeptide Aminopeptidase N Inhibitors with A Cyclic Imide Skeleton, J. Enzyme Inhibition, vol. 14 (1999) pp. 259-275.

Shisheva, Assia, et al., Insulinlike Effects of Zinc Ion in Vitro and in Vivo; Preferential Effects on Desensitized Adipocytes and Induction of Normoglycemia in Streptozocin-Induced Rats, Diabetes, vol. 41 (1992), pp. 982-988.

Sinyak, R. S. et al., Synthesis and Biological Properties of Derivatives of 4-Heterylmercaptoquinazoline, Translated from Khimikofarmatsevticheskii Zhurnal, vol. 20, No. 2, pp. 168-171 (1986), pp. 103-105.

Sokal, Joseph E., Basal Plasma Glucagon Levels of Man, Journal of Clinical Investigation, vol. 46, No. 5 (1967) pp. 778-785.

Soliman et al. Journal of the Chemical Society of Pakistan (1986), 8(2), 97-106. (Abstract 2 pages).

Somasekhara et al. Indian Journal of Pharmacey (1972), 34(5), 121-2.

Srivastava, P.P. et al., Efficacy of Centpiperalone in Combination With Biguanide & Sulfonylurea, Indian Journal of Experimental Biology, vol. 21 (1983), pp. 390-392.

Sun et al. CAPLUS Abstract 128:257413 (1998).

Tam, S. Y-K, et al.: "Nucleosides 112. Synthesis of Some New Pyrazolo-1 5-A-1 3 5-Triazines and Their C Nucleosides" Journal of Organic Chemistry, vol. 44, No. 25, 1979, pp. 4547-4553, XP002390906.

Tanaka, Keiji et al, Vanadate Inhibits the ATP-Dependant Degradation of Proteins in Reticulocytes Without Affecting Ubiquitin Conjugation, The Journal of Biological Chemistry, vol. 259, No. 4 (1983), 2803-2809.

Van Heeswijk et al., PubMed Abstract (Antivir Ther. 6(4);2001-29) Dec. 2001.

Villhauer, Edwin B. et al., 1-[[(3-Hydroxy-1-adamantyl)amino]acetyl]-2-cyano-(S)-pyrrolidine: A Potent, Selective, and Orally Bioavailable Dipeptidyl Peptidase IV Inhibitor with Antihyperglycemic Properties, J. Med. Chem. 46 (2003), pp. 2774-2789.

Villhauer, Edwin B. et al., DPP-IV Inhibition and Therapeutic Potential, Annual Reports in Chemistry 36 (2001), 191-200.

Vippagunta et al, Advanced Drug Delivery Reviews 48: 3-26, 2001.

Wang, F. et al.: "A novel Synthesis of Aryl[1,2-a]pyrazine Derivatives" Molecules, Molecular Diversity Preservation International, BASEL, CH, vol. 9, May 2004, pp. 574-582, XP002390904.

Weber, A.E.: Dipeptidyl Peptidase IV Inhibitors for the Treatment of Diabetes, Journal of Medicinal Chemistry, vol. 47, 2004 pp. 4135-4141, XP002329845.

West, Antony R., Solid State Chemistry and its Applictions, Wile, New York, 1988, pp. 358 & 365.

Wolf et al., CAPLUS Abstract 115: 114452 (1991).

Wolf Manfred E. "Burger's Medicinal Chemistry, 5ed, Part 1" John Wiley and Sons. 1995, pp. 975-977.

XP002310117 Database Crossfire Beilstein Institut Zur Foerderung Der Chmischen Wissenschaften. XP002310117. Beilstein Registry No. 8373244 & KHIM. Geterotsikl. Soedin., No. 8, 1998, pp. 1125-1129.

XP002310118 Database Crossfire Beilstein Institut Zur Foerderung Der Chmischen Wissenschaften. XP002310118. Beilstein Registry No. 7643826 & KHIM. Geterotsikl. Soedin., vol. 32, No. 5, 1996, pp. 703-707.

XP002310119 Database Crossfire Beilstein Institut Zur Foerderung Der Chmischen Wissenschaften. XP002310119. Beilstein Registry No. 649497 & J. Pharm. Sci. vol. 80, No. 7, 1991, pp. 705-706.

XP002310120 Database Crossfire Beilstein Institut Zur Foerderung Der Chmischen Wissenschaften. XP002310120. Beilstein Registry No. 638238 & Synthetic Procedures in Nucleic Acid Chemistry, vol. 1, 1968, p. 92.

XP002310121 Database Crossfire Beilstein Institut Zur Foerderung Der Chmischen Wissenschaften. XP002310121. Beilstein Registry No. 7289032 & Nucleosides Nucleotides, Vol. 14, No. 3-5, 1995, pp. 653-656.

XP002311761 Database CA Online Chemical Abstracts Service, Columbus, OH, US; Troschuetz, Reinhard et al., The reaction of O-functional benzylmalononitriles with N-bisnucleophiles as well as alcoholates. XP002311761 retrieved from STN Database accession No. 1994:217538 abstract & Archiv Der Pharmazie (Winheim, Germany), 326(11), 865-9 Coden: ARPMAS; ISSN: 0365-6233, 1993.

XP002335063 Database Crossfire Beilstein Institut zur Foerderung der Wissenschaften, Franfurt am Main, DE: XP002335063. Database-Accession No. 1525341 & J. Heterocycl.Chem., vol. 12, 1975, pp. 683-687.

XP002335064 Database Crossfire Beilstein Institut zur Foerderung der Wissenschaften, Frankfurt am Main, DE: XP002335064. Database Accession No. 1447881 & J. Heterocycl.Chem., vol. 305,1972, pp. 724-730.

XP002335065 Database Crossfire Beilstein Institut zur Foerderung der Wissenchaften, Frankfurt am Main, DE; XP002335065. Database Accession No. 1447134 & J.Org.Chem., vol. 43, 1978, pp. 4069-4074.

XP002335066 Database Crossfire Beilstein Institut zur Foerderung der Wissenchaften, Frankfurt am Main, DE; XP002335066. Database Accession No. 386682 & J.Chem.Soc., 1952, pp. 4985-4990.

XP002335067 Database Crossfire Beilstein Institut zur Foerderung der Wissenchaften, Frankfurt am Main, DE; XP002335067. Database Accession No. 389575 & Chem.Ber., vol. 88, 1968, pp. 106-109.

XP002335068 Database Crossfire Beilstein Institut zur Foerderung der Wissenchaften, Frankfurt am Main, DE; XP002335068. Database Accession No. 472441 & Yakugaku Zasshi, vol. 88, 1968, pp. 106-109.

XP002335069 Database Crossfire Beilstein Institut zur Foerderung der Wissenchaften, Frankfurt am Main, DE; XP002335069. Database Accession No. 1447840 & Chem.Ber., vol. 101, No. 8, 1968, pp. 2679-2689.

XP002335070 Database Crossfire Beilstein Institut zur Foerderung der Wissenchaften, Frankfurt am Main, DE; XP002335070. Database Accession No. 1448669 & Chem.Ber., vol. 101, No. 8, 1968, pp. 2679-2689.

XP002335071 Database Crossfire Beilstein Institut zur Foerderung der Wissenchaften, Frankfurt am Main, DE; XP002335071. Database Accession No. 4991064, J.Chem.Soc.Perkin Trans.1, 1980, pp. 1370-1380.

XP002335072 Database Crossfire Beilstein Institut zur Foerderung der Wissenchaften, Frankfurt am Main, DE; XP002335072. Database Accession No. 990008, J.Prakt.Chem., vol. 315, 1973, pp. 1166-1168.

XP002335073 Database Crossfire Beilstein Institut zur Foerderung der Wissenchaften, Frankfurt am Main, DE; XP002335073. Database Accession no. 6219070, J.Prakt.Chem., vol. 330, No. 2, 1988, pp. 323-324.

XP002335074 Database Crossfire Beilstein Institut zur Foerderung der Wissenchaften, Frankfurt am Main, DE; XP002335074. Database Accession No. 392446, J.Heterocycl.Chem., vol. 8, 1971, pp. 367-371.

XP002335075 Database Crossfire Beilstein Institut zur Foerderung der Wissenchaften, Frankfurt am Main, DE; XP002335075. Database Accession No. 4742608, J. Prakt.Chem., vol. 333, No. 1, 1991, pp. 149-151.

XP002335076 P002335076 Database Crossfire Beilstein Institut zur Foerderung der Wissenschaften, Frankfurt am Main, DE; XP002335076. Database Accession No. 490809, & Angew.Chem., vol. 84, 1972, p. 1185.

XP002392081 Database Biosis [Online] Biosciences Information Service, Philadelphia, PA, US; 1991, Bahaji E-H et al.: "Studies on Immunostimulating Derivatives Synthesis of Some Pyrrolo-1 2-C-Pyrimidines" XP002392081. Database accession No. PREV199192140000 abstract.

XP002392082 Database Beilstein [online] Beilstein Crossfire Institut Zur Forderung Der Chemischen Wissenschaften, DE; 1991, XP002392082. Database Accession No. BRN 5340228 abstract.

XP00239083 Database Beilstein [online] Beilstein Crossfire Institut Zur Foerderung Der Chemischen Wissenschaften, DE; Citation No. 5593678 1991, XP00239083.

XP002392084 Database CA [online] Chemical Abstract service, Columbus, Ohio, US; Reg No. 102482-94-0 Liu, Gang: "Fungal endophyte-epichloe and its secondary metabolites" XP002392084. Database Accession No. 2004:340837 abstract.

XP002392085 Database Beilstein [online] Beilstein Crossfire Institut Zur Foerderung Der Chemischen Wissenschaften, DE; 1924, XP002392085. Database Accession No. BRN 3799088 abstract.

XP002392086 Database Beilstein [online] Beilstein Corssfire Institut Zur Foerderung Der Chemischen Wissenschaften, DE; 1989 XP002392086. Database Accession No. BRN 5951213 abstract.

XP002392087 Database Beilstein [online] Beilstein Crossfire Institut Zur Foerderung Der Chemischen Wissenschaften, DE; 1960 XP002392087. Database Accession No. BRN 609897 abstract.

XP002392088 Database Beilstein [online] Beilstein Crossfire Institut Zur Foerderung Der Chemischen Wissenschaften, DE; 1993 XP002392088. Database Accession No. BRN 6139401 abstract.

XP002392089 Database Beilstein [online] Beilstein Crossfire Institut Zur Foererung Der Chemischen Wissenschaften DE; 1974 XP002392089. Database Accession No. BRN 514343 abstract.

Alagarsamy, V. et al. "Synthesis and pharmacological investigation . . . " Pharmazie, vol. 57, No. 5 2002, pp. 306-307, XP008084498 .

Algarsamy, V. et al. "Synthesis, analgesic, antii-inflammatory . . . " Bio & Pharm. Bulletin of Japan, Pharma society of JP, vol. 25, No. 11, 2002, pp. 1432-1435, XP008084513 ISSN: 0918-6158.

Barnickel et al. STN Printout (one page).

Desai N C et al "Synthesis and anti-Hiv . . . " Indian Journal of Experimental Bio., vol. 36, No. 12, 1998 pp. 1280-1283, XP008084509 ISSN: 0019-5889.

Kamata et al., CAPLUS Abstract 105: 191027, 1986 Chemical & Pharma Bulletin (1985), 33(8), 3160-75.

Kotani, T. et al., "Highly selective aldose reductase . . . " Journal of Medicinal Chem., American Chem. Society. Washington, US, vol. 40, No. 5, 1997, pp. 684-694 XP000652330.

Misra, V. et al. "Synthesis of N-aryl-n . . . " Pol. J. Pharmacol Pharm vol. 31, 1979, pp. 161-167, XP008084507.

Miyamura, K. et al. "Reaction of Copper (II) Complexes Optically . . . " J. Chem. Soc. Dalton Trans. 1987, pp. 1127-1132, XP008082357.

Schilling et al., CAPLUS 2005:1050865 DN 143:347172.

Sederaviciute et al., CAPLUS Abstract 125:300937 (1996).

Wang et al. "Studies of Quinazolinones . . . " Biorganic & Med hem.. Letters, Oxford, GB, vol. 12, No. 4, 2002, pp. 571-574, XP009077496 ISSN 0960-894X.

WEEKLY ADMINISTRATION OF DIPEPTIDYL PEPTIDASE INHIBITORS

RELATED APPLICATION

This application claims the benefit of U.S. Provisional Application No. 60/894,624 filed Mar. 13, 2007, which is incorporated herein by reference.

FIELD OF THE INVENTION

The invention relates to the method of administering compounds and pharmaceutical compositions used to inhibit dipeptidyl peptidase IV as well as treatment methods based on such administration.

DESCRIPTION OF RELATED ART

Dipeptidyl Peptidase IV (IUBMB Enzyme Nomenclature EC.3.4.14.5) is a type II membrane protein that has been referred to in the literature by a wide a variety of names including DPP4, DP4, DAP-IV, FAPβ, adenosine deaminase complexing protein 2, adenosine deaminase binding protein (ADAbp), dipeptidyl aminopeptidase IV; Xaa-Pro-dipeptidyl-aminopeptidase; Gly-Pro naphthylamidase; postproline dipeptidyl aminopeptidase IV; lymphocyte antigen CD26; glycoprotein GP110; dipeptidyl peptidase IV; glycylproline aminopeptidase; glycylproline aminopeptidase; X-prolyl dipeptidyl aminopeptidase; pep X; leukocyte antigen CD26; glycylprolyl dipeptidylaminopeptidase; dipeptidyl-peptide hydrolase; glycylprolyl aminopeptidase; dipeptidyl-aminopeptidase IV; DPP IV/CD26; amino acyl-prolyl dipeptidyl aminopeptidase; T cell triggering molecule Tp103; X-PDAP. Dipeptidyl Peptidase IV is referred to herein as "DPP-IV."

DPP-IV is a non-classical serine aminodipeptidase that removes Xaa-Pro dipeptides from the amino terminus (N-terminus) of polypeptides and proteins. DPP-IV dependent slow release of dipeptides of the type X-Gly or X-Ser has also been reported for some naturally occurring peptides.

DPP-IV is constitutively expressed on epithelial and endothelial cells of a variety of different tissues (intestine, liver, lung, kidney and placenta), and is also found in body fluids. DPP-IV is also expressed on circulating T-lymphocytes and has been shown to be synonymous with the cell-surface antigen, CD-26.

DPP-IV is responsible for the metabolic cleavage of certain endogenous peptides (GLP-1 (7-36), glucagon) in vivo and has demonstrated proteolytic activity against a variety of other peptides (GHRH, NPY, GLP-2, VIP) in vitro.

GLP-1 (7-36) is a 29 amino-acid peptide derived by post-translational processing of proglucagon in the small intestine. GLP-1 (7-36) has multiple actions in vivo including the stimulation of insulin secretion, inhibition of glucagon secretion, the promotion of satiety, and the slowing of gastric emptying. Based on its physiological profile, the actions of GLP-1 (7-36) are believed to be beneficial in the prevention and treatment of type II diabetes and potentially obesity. For example, exogenous administration of GLP-1 (7-36) (continuous infusion) in diabetic patients has been found to be efficacious in this patient population. Unfortunately, GLP-1 (7-36) is degraded rapidly in vivo and has been shown to have a short half-life in vivo ($t_{1/2}$=10.5 minutes).

Based on a study of genetically bred DPP-IV knock out mice and on in vivo/in vitro studies with selective DPP-IV inhibitors, DPP-IV has been shown to be the primary degrading enzyme of GLP-1 (7-36) in vivo. GLP-1 (7-36) is degraded by DPP-IV efficiently to GLP-1 (9-36), which has been speculated to act as a physiological antagonist to GLP-1 (7-36). Inhibiting DPP-IV in vivo is therefore believed to be useful for potentiating endogenous levels of GLP-1 (7-36) and attenuating the formation of its antagonist GLP-1 (9-36). Thus, DPP-IV inhibitors are believed to be useful agents for the prevention, delay of progression, and/or treatment of conditions mediated by DPP-IV, in particular diabetes and more particularly, type 2 diabetes mellitus, diabetic dislipidemia, conditions of impaired glucose tolerance (IGT), conditions of impaired fasting plasma glucose (IFG), metabolic acidosis, ketosis, appetite regulation and obesity.

Several compounds have been shown to inhibit DPP-IV. Nonetheless, a need still exists for new DPP-IV inhibitors and methods of administering such inhibitors for the treatment of disease.

SUMMARY OF THE INVENTION

A method is provided comprising: administering a weekly dose of between 1 mg/week and 500 mg/week of Compound I to a patient, optionally between 12.5 mg/week and 400 mg/week of Compound I, optionally between 20 mg/week and 400 mg/week of Compound I, optionally between 20 mg/week and 200 mg/week of Compound I, optionally between 50 mg/week and 400 mg/week of Compound I, and optionally between 100 mg/week and 400 mg/week of Compound I. In one variation, a weekly dose of 3.125 mg, 12.5 mg, 20 mg, 25 mg, 50 mg, 75 mg, 100 mg, 125 mg, 150 mg, 175 mg, 200 mg, 250 mg, 400 mg or 500 mg of Compound I is administered, optionally a weekly dose of 100 mg, 125 mg, 150 mg, 175 mg, 200 mg, 250 mg or 400 mg of Compound I is administered.

A method is also provided comprising administering a weekly dose of more than 250 mg of Compound I, optionally at least 275 mg of Compound I, optionally at least 300 mg of Compound I, optionally at least 350 mg of Compound I, and optionally at least 400 mg of Compound I to a patient. In one variation, the weekly dose of Compound I administered to the patient is not more than 500 mg. In another variation, the weekly dose of Compound I administered to the patient is not more than 400 mg. In still another variation, the weekly dose of Compound I administered to the patient is not more than 350 mg. In yet another variation, the weekly dose of Compound I administered to the patient is more than 250 mg and not more than 500 mg. In a further variation, the weekly dose of Compound I administered to the patient is more than 250 mg and not more than 400 mg. In other variations, a weekly dose of 275 mg, 300 mg, 350 mg, 400 mg or 500 mg of Compound I is administered to a patient.

In still a further variation, administering is performed 1 time per week and may optionally be performed 1 time per week as a single dosage. Optionally, administering is performed 1 time per week for a period of at least 1 month, optionally for a period of at least 2 months and optionally for a period of at least 3 months. In one variation, administering is performed in the morning and optionally is performed in the morning prior to a first meal of the day for the patient.

Administering may be performed by a wide range of routes of administration including, but not limited to a route selected from the group consisting of orally, parenterally, intraperitoneally, intravenously, intraarterially, transdermally, sublingually, intramuscularly, rectally, transbuccally, intranasally, liposomally, via inhalation, vaginally, intraoccularly, via local delivery, subcutaneously, intraadiposally, intraarticularly, intraperitoneally and intrathecally. In one particular variation, administering is performed orally.

A method is also provided for administering Compound I in combination with one or more antidiabetic or incretin compounds other than Compound I. In one embodiment, such combination therapy method is performed where a weekly dose of between 1 mg/week and 500 mg/week of Compound I, optionally between 12.5 mg/week and 400 mg/week of Compound I, optionally between 20 mg/week and 400 mg/ of Compound I, optionally between 20 mg/week and 200 mg/week of Compound I, optionally between 50 mg/week and 400 mg/week of Compound I, and optionally between 100 mg/week and 400 mg/week of Compound I. In one variation, a weekly dose of 3.125 mg, 12.5 mg, 20 mg, 25 mg, 50 mg, 75 mg, 100 mg, 125 mg, 150 mg, 175 mg, 200 mg, 250 mg, 400 mg or 500 mg of Compound I is administered to a patient in combination with one or more antidiabetic compounds other than Compound I.

In a further variation, such combination therapy method is performed where a weekly dose of more than 250 mg of Compound I, optionally at least 275 mg of Compound I, optionally at least 300 mg of Compound I, optionally at least 350 mg of Compound I, and optionally at least 400 mg of Compound I is administered to a patient. In still a further variation, the weekly dose of Compound I administered to the patient is not more than 500 mg. In another variation, the weekly dose of Compound I administered to the patient is not more than 400 mg. In still another variation, the weekly dose of Compound I administered to the patient is not more than 350 mg. In yet another variation, the weekly dose of Compound I administered to the patient is more than 250 mg and not more than 500 mg. In a further variation, the weekly dose of Compound I administered to the patient is more than 250 mg and not more than 400 mg. In other variations, a weekly dose of 275 mg, 300 mg, 350 mg, 400 mg or 500 mg of Compound I is administered to a patient in combination with one or more antidiabetic compounds other than Compound I.

In regard to each of the above embodiments and variations thereof, Compound I may be administered as a free base or as a pharmaceutically acceptable salt thereof. In particular variations, Compound I is administered as a HCl, methanesulfonate, succinate, benzoate, toluenesulfonate, R-(−)-mandelate or benzenesulfonate salt of Compound I.

Pharmaceutical compositions are also provided. In one embodiment, a pharmaceutical composition is provided that is formulated in a single dose form wherein such single dose form comprises between 1 mg/week and 500 mg/week of Compound I, optionally between 12.5 mg/week and 400 mg/week of Compound I, optionally between 20 mg/week and 400 mg/ of Compound I, optionally between 20 mg/week and 200 mg/week of Compound I, optionally between 50 mg/week and 400 mg/week of Compound I, and optionally between 100 mg/week and 400 mg/week of Compound I. In particular variations, the pharmaceutical composition comprises 3.125 mg, 12.5 mg, 20 mg, 25 mg, 50 mg, 75 mg, 100 mg, 125 mg, 150 mg, 175 mg, 200 mg, 250 mg, 400 mg or 500 mg of Compound I.

In another embodiment, a pharmaceutical composition is provided that is formulated in a single dose form wherein such single dose form comprises more than 250 mg of Compound I, optionally at least 275 mg of Compound I, optionally at least 300 mg of Compound I, optionally at least 350 mg of Compound I, and optionally at least 400 mg of Compound I. In one variation, the pharmaceutical composition comprises not more than 500 mg of Compound I. In another variation, the pharmaceutical composition comprises not more than 400 mg of Compound I. In still another variation, the pharmaceutical composition comprises not more than 350 mg of Compound I. In yet another variation, the pharmaceutical composition comprises more than 250 mg and not more than 500 mg of Compound I. In a further variation, the pharmaceutical composition comprises more than 250 mg and not more than 400 mg of Compound I. In other variations, the pharmaceutical composition comprises 275 mg, 300 mg, 350 mg, 400 mg or 500 mg of Compound I.

In another embodiment, a pharmaceutical composition is provided that comprises Compound I and one or more antidiabetic or incretin compounds other than Compound I in a single dose form. In one variation, Compound I is present in the single dose form in a dosage amount between 1 mg/week and 500 mg/week of Compound I, optionally between 12.5 mg/week and 400 mg/week of Compound I, optionally between 20 mg/week and 400 mg/ of Compound I, optionally between 20 mg/week and 200 mg/week of Compound I, optionally between 50 mg/week and 400 mg/week of Compound I, and optionally between 100 mg/week and 400 mg/week of Compound I. In particular variations, the pharmaceutical composition comprises 3.125 mg, 12.5 mg, 20 mg, 25 mg, 50 mg, 75 mg, 100 mg, 125 mg, 150 mg, 175 mg, 200 mg, 250 mg, 400 mg or 500 mg of Compound I.

In another variation, Compound I is present in the single dose form in a dosage amount of more than 250 mg of Compound I, optionally at least 275 mg of Compound I, optionally at least 300 mg of Compound I, optionally at least 350 mg of Compound I, and optionally at least 400 mg of Compound I. In a further variation, the pharmaceutical composition comprises not more than 500 mg of Compound I. In another variation, the pharmaceutical composition comprises not more than 400 mg of Compound I. In still another variation, the pharmaceutical composition comprises not more than 350 mg of Compound I. In yet another variation, the pharmaceutical composition comprises more than 250 mg and not more than 500 mg of Compound I. In a further variation, the pharmaceutical composition comprises more than 250 mg and not more than 400 mg of Compound I. In other variations, the pharmaceutical composition comprises 275 mg, 300 mg, 350 mg, 400 mg or 500 mg of Compound I.

In regard to each of the above embodiments and variations thereof regarding pharmaceutical compositions, Compound I may be present in the pharmaceutical composition as a free base or as a pharmaceutically acceptable salt thereof. In particular variations, Compound I is present as a HCl, methanesulfonate, succinate, benzoate, toluenesulfonate, R-(−)-mandelate or benzenesulfonate salt of Compound I.

Also in regard to each of the above embodiments and variations thereof regarding pharmaceutical compositions, the pharmaceutical composition may optionally be a single dose form adapted for oral administration, optionally a solid formulation adapted for oral administration, and optionally a tablet or capsule adapted for oral administration. Further, in regard to each of the above embodiments and variations thereof regarding pharmaceutical compositions, the pharmaceutical composition may optionally be a single dose form adapted for parenteral (subcutaneous, intravenous, subdermal or intramuscular) administration, optionally a solution formulation adapted for parenteral administration, and optionally a suspension formulation adapted for parenteral administration. The pharmaceutical formulation may also be an extended release formulation adapted for oral administration.

Also in regard to each of the above embodiments and variations thereof regarding pharmaceutical compositions, the pharmaceutical composition may be employed to prevent or treat conditions mediated by DPP-IV such as diabetes and more particularly, type 2 diabetes mellitus; diabetic dislipidemia; impaired glucose tolerance (IGT); impaired fasting plasma glucose (IFG); metabolic acidosis; ketosis; appetite regulation; obesity; complications associated with diabetes including diabetic neuropathy, diabetic retinopathy and kidney disease; hyperlipidemia including hypertriglyceridemia, hypercholesteremia, hypoHDLemia and postprandial hyperlipidemia; arteriosclerosis; hypertension; myocardial infarction, angina pectoris, cerebral infarction, cerebral apoplexy and metabolic syndrome.

Combinations of Compound I with one or more antidiabetic or incretin compounds other than Compound I provide excellent effects such as 1) enhancement in therapeutic effects of Compound I and/or the antidiabetic or incretin compounds; 2) reduction in side effects of Compound I and/or the antidiabetic or incretin compounds; and 3) reduction in a dose of Compound I and/or the antidiabetic or incretin compounds. Accordingly, the present invention comprises methods of administering Compound I in combination with one or more other antidiabetic or incretin compounds and pharmaceutical compositions comprising Compound I together with one or more other antidiabetic or incretin compounds. It is noted that several different dosage ranges for particular antidiabetic and incretin compounds are provided herein. It is intended for the scope of the present invention to include drug combinations covering any of the disclosed ranges for Compound I in combination with any of the dosage ranges described herein for other antidiabetic or incretin compounds.

With respect to each of the above embodiments and variations thereof regarding methods and pharmaceutical compositions comprising one or more antidiabetic or incretin compounds other than Compound I, the one or more antidiabetic or incretin compounds may be selected from any of a variety of known antidiabetic and incretin compounds. In one variation, the one or more antidiabetic or incretin compounds used in combination with Compound I may optionally be selected from the group consisting of insulin signaling pathway modulators, compounds influencing a dysregulated hepatic glucose production, insulin sensitivity enhancers, and insulin secretion enhancers.

The one or more antidiabetic or incretin compounds used in combination with Compound I may also optionally be selected from the group consisting of protein tyrosine phosphatase inhibitors, glutamine-fructose-6-phosphate amidotransferase inhibitors, glucose-6-phosphatase inhibitors, fructose-1,6-bisphosphatase inhibitors, glycogen phosphorylase inhibitors, glucagon receptor antagonists, phosphoenolpyruvate carboxykinase inhibitors, pyruvate dehydrogenase kinase inhibitors, alpha-glucosidase inhibitors, inhibitors of gastric emptying, glucokinase activators, GLP-1 receptor agonists, GLP-2 receptor agonists, UCP modulators, RXR modulators, GSK-3 inhibitors, PPAR modulators, metformin, insulin, $\alpha_2$-adrenergic antagonists, deacetylases (e.g., reservatrol, sirtuin agonist, polyphenols), and Sodium dependent glucose transport (SGLT2) inhibitors.

The one or more antidiabetic or incretin compounds used in combination with Compound I may also optionally be selected from the group consisting of GSK-3 inhibitors, retinoid X receptor agonists, Beta-3 AR agonists, UCP modulators, antidiabetic thiazolidinediones, non-glitazone type PPAR gamma agonists, dual PPAR gamma/PPAR alpha agonists, antidiabetic vanadium containing compounds and biguanides.

The one or more antidiabetic or incretin compounds used in combination with Compound I may also optionally be thiazolidinediones selected from the group consisting of (S)-((3,4-dihydro-2-(phenyl-methyl)-2H-1-benzopyran-6-yl) methyl-thiazolidine-2,4-dione, 5-{[4-(3-(5-methyl-2-phenyl-4-oxazolyl)-1-oxo-propyl)-phenyl]-methyl}-thiazolidine-2,4-dione, 5-{[4-(1-methyl-cyclohexyl) methoxy)-phenyl]methyl]-thiazolidine-2,4-dione, 5-{[4-(2-(1-indolyl)ethoxy)phenyl]methyl}-thiazolidine-2,4-dione, 5-{4-[2-(5-methyl-2-phenyl-4-oxazoly)-ethoxy)]benzyl}-thiazolidine-2,4-dione, 5-(2-naphthylsulfonyl)-thiazolidine-2,4-dione, bis{4-[(2,4-dioxo-5-thiazolidinyl)-methyl]phenyl}methane, 5-{4-[2-(5-methyl-2-phenyl-4-oxazolyl)-2-hydroxyethoxy]-benzyl}--thiazolidine-2,4-dione, 5-[4-(1-phenyl-1-cyclopropanecarbonylamino)-benzyl]-thiazolidine-2,4-dione, 5-{[4-(2-(2,3-dihydroindol-1-yl) ethoxy)phenylmethyl]-thiazolidine-2,4-dione, 5-[3-(4-chloro-phenyl])-2-propynyl]-5-phenylsulfonyl)thiazolidine-2,4-dione, 5-[3-(4-chlorophenyl])-2-propynyl]-5-(4-fluorophenyl-sulfonyl)thiazolidine-2,4-dione,5-{[4-(2-(methyl-2-pyridinyl-amino)-ethoxy)phenyl]methyl}-thiazolidine-2,4-dione, 5-{[4-(2-(5-ethyl-2-pyridyl)ethoxy) phenyl]-methyl}-thiazolidine-2,4-dione, 5-{[4-((3,4-dihydro-6-hydroxy-2,5,7,8-tetramethyl-2H-1-benzopyran-2-yl)methoxy)-phenyl]-methyl)-thiazolidine-2,4-dione, 5-[6-(2-fluoro-benzyloxy)-naphthalen-2-ylmethyl]-thiazolidine-2,4-dione, 5-([2-(2-naphthyl)-benzoxazol-5-yl]-methyl}thiazolidine-2,4-dione and 5-(2,4-dioxothiazolidin-5-ylmethyl)-2-methoxy-N-(4-trifluoromethyl-benzyl) benzamide, including any pharmaceutically acceptable salts thereof.

In one variation, the one or more antidiabetic compounds used in combination with Compound I includes metformin. In one particular variation, the metformin in this combination comprises one or more pharmaceutically acceptable salts thereof. In another particular variation, the metformin in this combination comprises a metformin HCl salt. In still another particular variation, the metformin in this combination is administered in a daily dose of between 125 and 2550 mg. In yet another variation, the metformin in this combination is administered in a daily dose of between 250 and 2550 mg. In other variations, the metformin in this combination is administered in an immediate release or an extended release formulation.

In another variation, the one or more antidiabetic compounds used in combination with Compound I includes one or more sulphonyl urea derivatives.

The one or more antidiabetic compounds used in combination with Compound I may also optionally be selected from the group consisting of glisoxepid, glyburide, glibenclamide, acetohexamide, chloropropamide, glibornuride, tolbutamide, tolazamide, glipizide, carbutamide, gliquidone, glyhexamide, phenbutamide, tolcyclamide, glimepiride and gliclazide, including any pharmaceutically acceptable salts thereof. In one variation, the one or more antidiabetic compounds administered in combination with Compound I includes glimepiride.

The one or more antidiabetic compounds used in combination with Compound I may also optionally be selected from the group consisting of incretin hormones or mimics thereof, beta-cell imidazoline receptor antagonists, and short-acting insulin secretagogues.

In another variation, the one or more antidiabetic compounds used in combination with Compound I includes insulin.

The one or more antidiabetic compounds used in combination with Compound I may also optionally be one or more GLP-1 agonists including, for example, extendatide.

The one or more antidiabetic compounds used in combination with Compound I may also optionally be one or more GLP-2 agonists including, for example, human recombinant GLP-2.

The one or more antidiabetic compounds used in combination with Compound I may also optionally be one or more antidiabetic D-phenylalanine derivatives.

The one or more antidiabetic compounds used in combination with Compound I may also optionally be selected from the group consisting of repaglinide, mitiglinide and nateglinide, including any pharmaceutically acceptable salts thereof. In one variation, the one or more antidiabetic compounds administered in combination with Compound I includes mitiglinide calcium salt hydrate.

The one or more antidiabetic compounds used in combination with Compound I may also optionally be one or more alpha-Glucosidase inhibitors.

The one or more antidiabetic compounds used in combination with Compound I may also optionally be selected from the group consisting of acarbose, voglibose and miglitol, including any pharmaceutically acceptable salts thereof. In one variation, the one or more antidiabetic compounds administered in combination with Compound I includes voglibose. In another variation, the voglibose in this combination is administered in a daily dose of between 0.1 and 1 mg.

The one or more antidiabetic compounds used in combination with Compound I may also optionally be rosiglitazone, including any pharmaceutically acceptable salts thereof. In one variation, the rosiglitazone in this combination comprises a rosiglitazone maleate salt The one or more antidiabetic compounds used in combination with Compound I may also optionally be tesaglitazar, muraglitazar or naveglitazar, including any pharmaceutically acceptable salts thereof.

The one or more antidiabetic compounds used in combination with Compound I may also optionally be pioglitazone, including any pharmaceutically acceptable salts thereof. In one variation, the pioglitazone in this combination comprises a pioglitazone HCl salt. In another variation, the pioglitazone in this combination is administered in a daily dose of between 7.5 and 60 mg. In still another variation, the pioglitazone in this combination is administered in a daily dose of between 15 and 45 mg.

The one or more antidiabetic compounds used in combination with Compound I may also optionally comprise metformin and pioglitazone. In one variation, the pioglitazone in this combination comprises one or more pharmaceutically acceptable salts thereof. In another variation, the pioglitazone in this combination comprises a pioglitazone HCl salt. In still another variation, the pioglitazone in this combination is administered in a daily dose of between 7.5 and 60 mg. In yet another variation, the pioglitazone in this combination is administered in a daily dose of between 15 and 45 mg. In another variation of each of the above variations, the metformin in this combination comprises one or more pharmaceutically acceptable salts thereof. In one particular variation, the metformin in this combination comprises a metformin HCl salt. In another particular variation, the metformin in this combination is administered in a daily dose of between 125 and 2550 mg. In still another variation, the metformin in this combination is administered in a daily dose of between 250 and 2550 mg.

Compound I and pharmaceutical compositions comprising Compound I may be used to treat a range of diseases. In one variation, administering Compound I or a pharmaceutical composition comprising Compound I is performed to treat type I or type II diabetes disease state of the patient. In another variation, administering Compound I or a pharmaceutical composition comprising Compound I is performed to treat a pre-diabetic patient. In still another variation, administering Compound I or a pharmaceutical composition comprising Compound I is performed to treat an inflammatory bowel disease, Crohn's disease, chemotherapy-induced enteritis, oral mucositis or Shortened Bowel syndrome. In yet another variation, administering Compound I or a pharmaceutical composition comprising Compound I is performed to increase engraftment efficiency after bone marrow transplantation. In another variation, administering Compound I or a pharmaceutical composition comprising Compound I is performed to treat a patient suffering from conditions mediated by DPP-IV such as diabetes and more particularly, type 2 diabetes mellitus; diabetic dyslipidemia; impaired glucose tolerance (IGT); impaired fasting plasma glucose (IFG); metabolic acidosis; ketosis; appetite regulation; obesity; complications associated with diabetes including diabetic neuropathy, diabetic retinopathy and kidney disease; hyperlipidemia including hypertriglyceridemia, hypercholesteremia, hypoHDLemia and postprandial hyperlipidemia; arteriosclerosis; hypertension; myocardial infarction, angina pectoris, cerebral infarction, cerebral apoplexy and metabolic syndrome.

In addition, Compound I and pharmaceutical compositions comprising Compound I may be employed to prevent or treat conditions mediated by DPP-IV such as diabetes and more particularly, type 2 diabetes mellitus; diabetic dyslipidemia; impaired glucose tolerance (IGT); impaired fasting plasma glucose (IFG); metabolic acidosis; ketosis; appetite regulation; obesity; complications associated with diabetes including diabetic neuropathy, diabetic retinopathy and kidney disease; hyperlipidemia including hypertriglyceridemia, hypercholesteremia, hypoHDLemia and postprandial hyperlipidemia; arteriosclerosis; hypertension; myocardial infarction, angina pectoris, cerebral infarction, cerebral apoplexy and metabolic syndrome.

Also provided are kits comprising multiple doses of pharmaceutical compositions according to the present invention. In one variation, the kits further comprise instructions which comprise one or more forms of information selected from the group consisting of indicating a disease state for which the pharmaceutical composition is to be administered, storage information for the pharmaceutical composition, dosing information and instructions regarding how to administer the pharmaceutical composition.

Also provided are articles of manufacture comprising multiple doses of pharmaceutical composition according to the present invention. In one variation, the articles of manufacture further comprise packaging materials such as a container for housing the multiple doses of the pharmaceutical composition and or a label indicating one or more members of the group consisting of a disease state for which the compound is to be administered, storage information, dosing information and/or instructions regarding how to administer the composition.

It is noted in regard to all of the above embodiments that the embodiments should be interpreted as being open ended in the sense that the methods may comprise further actions beyond those specified including the administration of other pharmaceutically active materials to a patient. Similarly, unless otherwise specified, the pharmaceutical compositions, kits and articles of manufacture may further include other materials including other pharmaceutically active materials.

DEFINITIONS

Figure 1:
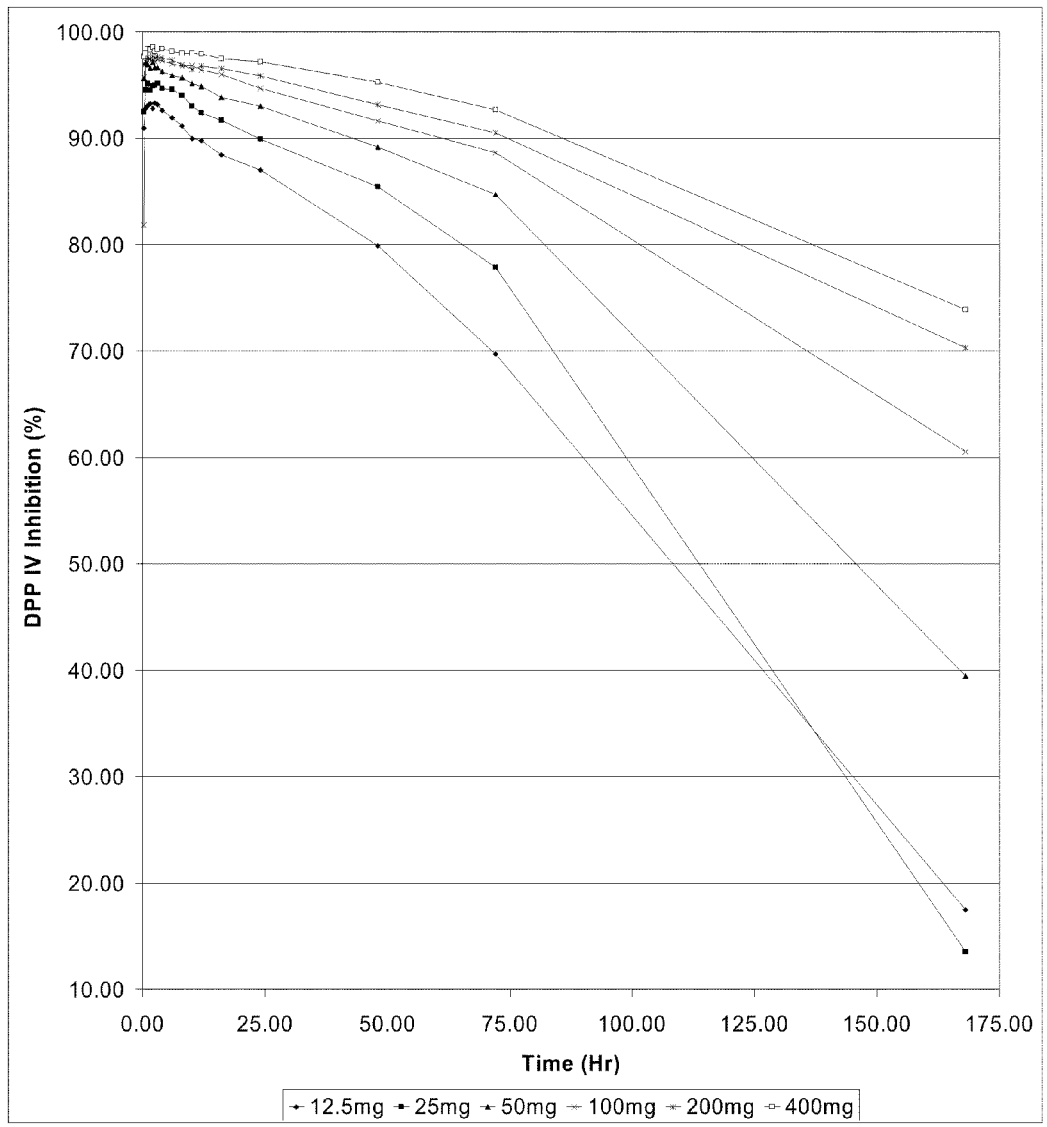
FIG. 1 illustrates DPP IV inhibition in plasma after a single oral administration of Compound I in human.

Unless otherwise stated, the following terms used in the specification and claims shall have the following meanings for the purposes of this Application.

"Disease" specifically includes any unhealthy condition of an animal or part thereof and includes an unhealthy condition that may be caused by, or incident to, medical or veterinary therapy applied to that animal, i.e., the "side effects" of such therapy.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts which are pharmaceutically acceptable, as defined above, and which possess the desired pharmacological activity. Such salts include, but are not limited to, acid addition salts formed with inorganic acids such as hydrochloric acid, hydrobromic acid, sulfuric acid, nitric acid, phosphoric acid, and the like; or with organic acids such as acetic acid, trifluoroacetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include, but are not limited to, base addition salts which may be formed when acidic protons present are capable of reacting with inorganic or organic bases. Acceptable inorganic bases include, but are not limited to, sodium hydroxide, sodium carbonate, potassium hydroxide, aluminum hydroxide and calcium hydroxide. Acceptable organic bases include, but are not limited to, ethanolamine, diethanolamine, triethanolamine, tromethamine, N-methylglucamine and the like.

"Subject" and "patient" includes humans, non-human mammals (e.g., dogs, cats, rabbits, cattle, horses, sheep, goats, swine, deer, and the like) and non-mammals (e.g., birds, and the like).

"Therapeutically effective amount" means that amount of a compound which, when administered to an animal for treating a disease, is sufficient to effect such treatment for the disease.

"Treatment" or "treating" means any administration of a therapeutically effective amount of a compound and includes:

(1) preventing the disease from occurring in an animal which may be predisposed to the disease but does not yet experience or display the pathology or symptomatology of the disease, (2) inhibiting the disease in an animal that is experiencing or displaying the pathology or symptomatology of the disease (i.e., arresting further development of the pathology and/or symptomatology), or (3) ameliorating the disease in an animal that is experiencing or displaying the pathology or symptomatology of the disease (i.e., reversing the pathology and/or symptomatology).

DETAILED DESCRIPTION OF THE INVENTION 1. 2-[6-(3-amino-piperidin-1-yl)-3-methyl-2,4-dioxo-3,4-dihydro-2H-pyrimidin-1-ylmethyl]-4-fluoro-benzonitrile and compositions thereof The present invention relates generally to the administration of 2-[6-(3-Amino-piperidin-1-yl)-3-methyl-2,4-dioxo-3,4-dihydro-2H-pyrimidin-1-ylmethyl]-4-fluoro-benzonitrile (referred to herein as "Compound I") whose structure is provided below.

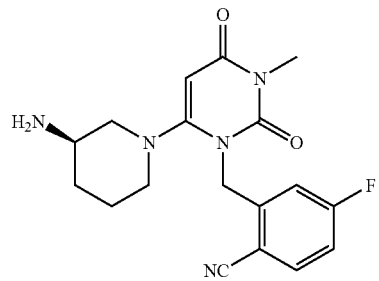

Example 1 describes one method for synthesizing Compound I. It is noted that other methods for synthesizing Compound I may be used as would be appreciated to one of ordinary skill in the art. As described in detail below, Compound I has long acting DPP-IV inhibitory affects.

Compound I may be administered in its free base form and may also be administered in the form of salts, hydrates and prodrugs that are converted in vivo into the free base form of Compound I. For example, it is within the scope of the present invention to administer Compound I as a pharmaceutically acceptable salt derived from various organic and inorganic acids and bases in accordance with procedures well known in the art. As used herein, Compound I is intended to encompass salts, hydrates and prodrugs of Compound I unless otherwise specified.

A pharmaceutically acceptable salt of Compound I preferably confers improved pharmacokinetic properties as compared to the free base form of Compound I. Pharmaceutically acceptable salts may also confer desirable pharmacokinetic properties on Compound I that it did not previously possess, and may even positively affect the pharmacodynamics of the compound with respect to its therapeutic activity in the body.

Particular examples of salts, hydrates and prodrugs of Compound I include, but are not limited to salt forms formed by inorganic or organic acids, e.g., hydrohalides such as hydrochloride, hydrobromide and hydroiodide; other mineral acids and their corresponding salts such as sulfate, nitrate, phosphate, etc.; alkyl and monoarylsulfonates such as ethanesulfonate, toluenesulfonate and benzenesulfonate; and other organic acids and their corresponding salts such as acetate, trifluoroacetate, tartrate, maleate, succinate, citrate, benzoate, salicylate and ascorbate. Further acid addition salts include, but are not limited to: adipate, alginate, arginate, aspartate, bisulfate, bisulfite, bromide, butyrate, camphorate, camphorsulfonate, caprylate, chloride, chlorobenzoate, cyclopentanepropionate, digluconate, dihydrogenphosphate, dinitrobenzoate, dodecylsulfate, fumarate, galacterate (from mucic acid), galacturonate, glucoheptaoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, iso-butyrate, lactate, lactobionate, malate, malonate, mandelate, metaphosphate, methanesulfonate, methylbenzoate, monohydrogenphosphate, 2-naphthalenesulfonate, nicotinate, nitrate, oxalate, oleate, pamoate, pectinate, persulfate, phenylacetate, 3-phenylpropionate, phosphate, phosphonate and phthalate.

In particular variations, Compound I is administered as a HCl, methanesulfonate, succinate, benzoate, toluenesulfonate, R-(−)mandelate or benzenesulfonate salt of Compound I. Example 1 describes the preparation of various salt forms of Compound I including TFA, HCl, benzoic, p-toluenesulfonic, succinic, R-(−)-mandelic and benzenesulfonic acid salts.

2. Administration and Use of Compound I

The present invention relates generally to a method comprising administering Compound I to a patient at a weekly dose of between 1 mg/week and 500 mg/week of Compound I to a patient, optionally between 12.5 mg/week and 400 mg/week of Compound I, optionally between 20 mg/week and 400 mg/week of Compound I, optionally between 20 mg/week and 200 mg/week of Compound I, optionally between 50 mg/week and 400 mg/week of Compound I, and optionally between 100 mg/week and 400 mg/week of Compound. Specific dosage amounts that may be used include, but are not limited to 3.125 mg, 12.5 mg, 20 mg, 25 mg, 50 mg, 75 mg, 100 mg, 125 mg, 150 mg, 175 mg, 200 mg, 250 mg, 400 mg and 500 mg of Compound I per week. It is noted that unless otherwise specifically specified, Compound I may be administered in its free base form or as a pharmaceutically acceptable salt. However, the dosage amounts and ranges provided herein are always based on the molecular weight of the free base form of Compound I.

The present invention also relates generally to a method comprising administering Compound I to a patient at a weekly dose of more than 250 mg of Compound I, optionally at least 275 mg of Compound I, optionally at least 300 mg of Compound I, optionally at least 350 mg of Compound I, and optionally at least 400 mg of Compound I. In one variation, the weekly dose of Compound I administered to the patient is not more than 500 mg. In another variation, the weekly dose of Compound I administered to the patient is not more than 400 mg. In still another variation, the weekly dose of Compound I administered to the patient is not more than 350 mg. In yet another variation, the weekly dose of Compound I administered to the patient is more than 250 mg and not more than 500 mg. In a further variation, the weekly dose of Compound I administered to the patient is more than 250 mg and not more than 400 mg. In other variations, a weekly dose of 275 mg, 300 mg, 350 mg, 400 mg or 500 mg of Compound I is administered to the patient. It is noted that unless otherwise specifically specified, Compound I may be administered in its free base form or as a pharmaceutically acceptable salt. However, the dosage amounts and ranges provided herein are based on the molecular weight of the free base form of Compound I.

Compound I may be administered by any route of administration. In particular embodiments, however, the method of the present invention is practiced by administering Compound I orally. This type of administration is advantageous in that it is easy and may be self-administered by the patient.

Compound I may be administered one or more times per week. An advantage of the present invention, however, is that Compound I can be effectively administered at the dosage levels specified herein one time per week and may also be administered as a single dosage form one time a week. By being able to administer Compound I at the dosage levels specified herein only one time per week and orally, it is easier for patients to self-administer Compound I, thus improving the compliance of usage among patients requiring in vivo inhibition of DPP-IV activity.

Advantageously, Compound I is suitable for prolonged continuous use and may be administered to patients for an extended period of time. Accordingly, the method may be performed where Compound I is administered to a patient each week (optionally 1 time weekly) for a period of at least 1 month, optionally for at least 2 months, optionally for at least 3 months, and, if necessary, optionally for the duration of the patients disease profile.

Advantageously, Compound I may be administered at any time during the day. Optionally, Compound I is administered one time per week where administration occurs in the morning before meals. Because Compound I can stimulate insulin secretion when blood glucose levels reach 100 mg/dl and above, it may be beneficial to have Compound I in systemic circulation before an elevation in blood glucose levels occurs postprandially.

Figure 2:
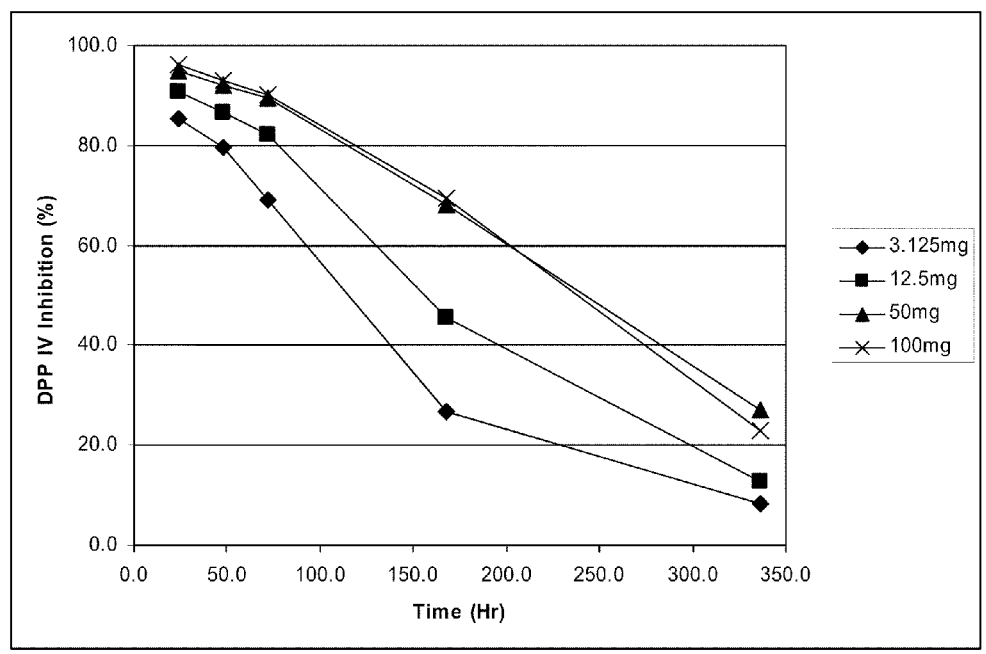
FIG. 2 illustrates DPP IV inhibition in plasma after a single oral administration of Compound I in human.

Compound I may be administered to any patient who would benefit from a course of treatment leading to the reduction of in vivo DPP-IV activity. As described in detail below, FIGS. 1 and 2 illustrate the observed effect that administering Compound I has on human plasma DPP-IV activity after a single oral administration. As can be seen from the data shown in FIG. 1, by administering Compound I at the dosage levels specified herein, Compound I can be effectively used relative to disease states where it is desired to reduce plasma DPP-IV activity. In view of the data presented, it is believed that when at least 12.5 mg of Compound I is administered to a patient, the patient's plasma DPP-IV activity may be reduced by greater than 10% relative to baseline for a period of at least 168 hours following administration; when at least 50 mg of Compound I is administered to a patient, the patient's plasma DPP-IV activity may be reduced by greater than 35% relative to baseline for a period of at least 168 hours following administration; and when 200 mg or 400 mg of Compound I is administered to a patient, the patient's plasma DPP-IV activity may be reduced by greater than 70% relative to baseline for a period of at least 168 hours following administration.

Examples of particular applications for administering Compound I include, but are not limited to the prevention, delay of progression, and/or treatment of conditions mediated by DPP-IV, in particular diabetes and more particularly, type 2 diabetes mellitus, diabetic dislipidemia, impaired glucose tolerance (IGT), impaired fasting plasma glucose (IFG), metabolic acidosis, ketosis, appetite regulation, obesity and complications associated with diabetes including diabetic neuropathy, diabetic retinopathy, inflammatory bowel disease, Crohn's disease, chemotherapy-induced enteritis, oral mucositis, Shortened Bowel Syndrome and kidney disease. The conditions mediated by DPP-IV further includes hyperlipidemia such as hypertriglyceridemia, hypercholesteremia, hypoHDLemia and postprandial hyperlipidemia; arteriosclerosis; hypertension; myocardial infarction, angina pectoris, cerebral infarction, cerebral apoplexy and metabolic syndrome.

It is believed that administration of Compound I to type I or type II diabetic patients following a minimum treatment of at least 30 days will improve one or more cardiovascular measurements. It is also believed that administration of Compound I in combination with one or more antidiabetic or incretin compounds to type I or type II diabetic patients following a minimum treatment of at least 30 days will improve one or more cardiovascular measurements. Examples of cardiac measurements that may be improved include, but are not limited to a decrease in mean systolic blood pressure, an increase in HDL cholesterol, improvement in LDL/HDL ratio and a reduction in triglycerides.

It is also believed that administration of Compound I in combination with one or more antidiabetic or incretin compounds to patients with gastrointestinal inflammatory disorders (including, but not be limited to inflammatory bowel disease, Crohn's disease, chemotherapy-induced enteritis, oral mucositis and Shortened Bowel Syndrome) following a minimum treatment of at least 30 days will improve the health of the mucosal lining of the gastrointestinal tract. Improvement in the health of the mucosal lining of the gastrointestinal tract may be demonstrated by, but is not limited to, an increase in the intestinal surface area, reduced inflammation, and/or increases in absorption of nutrients.

Administering Compound I, one time per week at the dosage levels specified herein, to a patient with type 2 diabetes may also be beneficial. Patients receiving Compound I may also have a malfunction in insulin secretion from pancreatic islets rather than patients who have developed insulin resistance in peripheral insulin sensitive tissues/organs.

Advantageously, administering Compound I one time per week, at the dosage levels specified herein may also be used to treat patients who are prediabetic. It is believed that administering Compound I in a patient who is prediabetic serves to delay development of type II diabetes in that patient. Sustained increase in blood glucose desensitizes pancreatic islet function and impairs insulin secretion. By improving cyclic AMP levels and the calcium dynamics in beta cells, the cells activate genes repairing damaged cell components and are less vulnerable to glucose toxicity.

Administering Compound I one time per week, at the dosage levels specified herein is expected to have a range of desirous biological effects in vivo. For example, administering Compound I one time per week, at the dosage levels specified herein reduces the patient's blood glucose level when compared with placebo control. Such a decrease in postprandial blood glucose levels helps diabetic patients to maintain lower glucose levels.

Administering Compound I one time per week, at the dosage levels specified herein is also expected to have the affect of increasing the patient's insulin level or insulin sensitivity. Insulin facilitates entry of glucose into muscle, adipose and several other tissues. The mechanism by which cells can take up glucose is by facilitated diffusion through stimulation of insulin receptor. C-peptide and insulin are protein chains created by the activation and division of proinsulin (an inactive precursor to insulin). C-peptide and insulin are created and stored in the beta cells of the pancreas. When insulin is released into the bloodstream, equal amounts of C-peptide also are released. This makes C-peptide useful as a marker of insulin production. Administering Compound I according to the present invention is expected to increase the patient's C-peptide level.

Administering Compound I one time per week at the dosage levels specified herein is also expected to have the affect of decreasing the patient's hemoglobin A1c level by greater than 0.5% when compared to placebo control after extended treatment with Compound I. Further, administering Compound I one time per week at the dosage levels specified herein is also expected to have the affect of decreasing the patient's hemoglobin A1c level by greater than 0.2% when compared to placebo control after extended treatment with Compound I. Hb-A1c values are known to be directly proportional to the concentration of glucose in the blood over the life span of the red blood cells. Hb-A1c thus gives an indication of a patient's blood glucose levels over the previous last 90 days, skewed to the most recent 30 days. The observed reduction in the patient's hemoglobin A1c level thus verifies the sustained reduction in the patient's blood glucose levels as a result of administering Compound I one time per day at the dosage levels specified herein.

3. Combination Therapy Including Compound I

The present invention also relates to the use of Compound I in combination with one or more other antidiabetic and/or incretin compounds. Examples of such other antidiabetic compounds include, but are not limited to insulin signaling pathway modulators, like protein tyrosine phosphatase (PTPase) inhibitors, and glutamine-fructose-6-phosphate amidotransferase (GFAT) inhibitors; compounds influencing a dysregulated hepatic glucose production, like glucose-6-phosphatase (G6Pase) inhibitors, fructose-1,6-bisphosphatase (F-1,6-BPase) inhibitors, glycogen phosphorylase (GP) inhibitors, glucagon receptor antagonists and phosphoenolpyruvate carboxykinase (PEPCK) inhibitors; pyruvate dehydrogenase kinase (PDHK) inhibitors; insulin sensitivity enhancers (insulin sensitizers); insulin secretion enhancers (insulin secretagogues); alpha-glucosidase inhibitors; inhibitors of gastric emptying; glucokinase activators, GLP-1 receptor agonists, GLP-2 receptor agonists, UCP modulators, RXR modulators, GSK-3 inhibitors, PPAR modulators, metformin, insulin; and $\alpha_2$-adrenergic antagonists. Compound I may be administered with such at least one other antidiabetic compound either simultaneously as a single dose, at the same time as separate doses, or sequentially (i.e., where one is administered before or after the other is administered).

Examples of PTPase inhibitors that may be used in combination with Compound I include, but are not limited to those disclosed in U.S. Pat. Nos. 6,057,316, 6,001,867, and PCT Publication Nos. WO 99/58518, WO 99/58522, WO 99/46268, WO 99/46267, WO 99/46244, WO 99/46237, WO 99/46236, and WO 99/15529.

Examples of GFAT inhibitors that may be used in combination with Compound I include, but are not limited to those disclosed in Mol. Cell. Endocrinol. 1997, 135(1), 67-77.

Examples of G6Pase inhibitors that may be used in combination with Compound I include, but are not limited to those disclosed in PCT Publication Nos. WO 00/14090, WO 99/40062 and WO 98/40385, European Patent Publication No. EP682024 and Diabetes 1998, 47, 1630-1636.

Examples of F-1,6-BPase inhibitors that may be used in combination with Compound I include, but are not limited to those disclosed in PCT Publication Nos. WO 00/14095, WO 99/47549, WO 98/39344, WO 98/39343 and WO 98/39342.

Examples of GP inhibitors that may be used in combination with Compound I include, but are not limited to those disclosed in U.S. Pat. No. 5,998,463, PCT Publication Nos. WO 99/26659, WO 97/31901, WO 96/39384 and WO9639385 and European Patent Publication Nos. EP 978279 and EP 846464.

Examples of glucagon receptor antagonists that may be used in combination with Compound I include, but are not limited to those disclosed in U.S. Pat. Nos. 5,880,139 and 5,776,954, PCT Publication Nos. WO 99/01423, WO 98/22109, WO 98/22108, WO 98/21957, WO 97/16442 and WO 98/04528 and those described in Bioorg Med. Chem. Lett 1992, 2, 915-918, J. Med. Chem. 1998, 41, 5150-5157, and J. Biol. Chem. 1999, 274; 8694-8697.

Examples of PEPCK inhibitors that may be used in combination with Compound I include, but are not limited to those disclosed in U.S. Pat. No. 6,030,837 and Mol. Biol. Diabetes 1994, 2, 283-99.

Examples of PDHK inhibitors that may be used in combination with Compound I include, but are not limited to those disclosed in J. Med. Chem. 42 (1999) 2741-2746.

Examples of insulin sensitivity enhancers that may be used in combination with Compound I include, but are not limited to GSK-3 inhibitors, retinoid X receptor (RXR) agonists, Beta-3 AR agonists, UCP modulators, antidiabetic thiazolidinediones (glitazones), non-glitazone type PPAR gamma agonists, dual PPAR gamma/PPAR alpha agonists, antidiabetic vanadium containing compounds and biguanides such as metformin.

Examples of GSK-3 inhibitors include, but are not limited to those disclosed in PCT Publication Nos. WO 00/21927 and WO 97/41854.

Examples of RXR modulators include, but are not limited to those disclosed in U.S. Pat. Nos. 4,981,784, 5,071,773, 5,298,429 and 5,506,102 and PCT Publication Nos. WO89/05355, WO91/06677, WO92/05447, WO93/11235, WO95/18380, WO94/23068, and WO93/23431.

Examples of Beta-3 AR agonists include, but are not limited to CL-316,243 (Lederle Laboratories) and those disclosed in U.S. Pat. No. 5,705,515 and PCT Publication Nos. WO 99/29672, WO 98/32753, WO 98/20005, WO 98/09625, WO 97/46556, and WO 97/37646.

Examples of UCP modulators include agonists of UCP-1, UCP-2 and UCP-3. Examples of UCP modulators include, but are not limited to those disclosed in Vidal-Puig et al., Biochem. Biophys. Res. Commun., Vol. 235(1) pp. 79-82 (1997).

Examples of antidiabetic, PPAR modulating thiazolidinediones (glitazones) include, but are not limited to, (S)-((3,4-dihydro-2-(phenyl-methyl)-2H-1-benzopyran-6-yl) methyl-thiazolidine-2,4-dione (englitazone), 5-{[4-(3-(5-methyl-2-phenyl-4-oxazolyl)-1-oxo-propyl)-phenyl]-methyl}-thiazolidine-2,4-dione (darglitazone), 5-{[4-(1-methyl-cyclohexyl)methoxy)-phenyl]methyl]-thiazolidine-2,4-dione (ciglitazone), 5-{[4-(2-(1-indolyl)ethoxy)phenyl] methyl}-thiazolidine-2,4-dione (DRF2189), 5-{4-[2-(5-methyl-2-phenyl-4-oxazolyl)-ethoxy)]benzyl}-thiazolidine-2,4-dione (BM-13.1246), 5-(2-naphthylsulfonyl)-thiazolidine-2,4-dione (AY-31637), bis{4-[(2,4-dioxo-5-thiazolidinyl)-methyl]phenyl}methane (YM268), 5-{4-[2-(5-methyl-2-phenyl-4-oxazolyl)-2-hydroxyethoxy]-benzyl}- -thiazolidine-2,4-dione (AD-5075), 5-[4-(1-phenyl-1-cyclopropanecarbonylamino)-benzyl]-thiazolidine-2,4-dione (DN-108) 5-{[4-(2-(2,3-dihydroindol-1-yl)ethoxy)phenylmethyl)-thiazolidine-2,4-dione, 5-[3-(4-chloro-phenyl])-2-propynyl]-5-phenylsulfonyl)thiazolidine-2,4-dione, 5-[3-(4-chlorophenyl])-2-propynyl]-5-(4-fluorophenyl-sulfonyl) thiazolidine-2,4-dione,5-{[4-(2-(methyl-2-pyridinyl-amino)-ethoxy)phenyl]methyl}-thiazolidine-2,4-dione (rosiglitazone), 5-{[4-(2-(5-ethyl-2-pyridyl)ethoxy)phenyl]-methyl}-thiazolidine-2,4-dione (pioglitazone; marketed under the trademark ACTOS™), 5-[6-(2-fluoro-benzyloxy)-naphthalen-2-ylmethyl]-thiazolidine-2,4-dione (MCC555), 5-([2-(2-naphthyl)-benzoxazol-5-yl]-methyl}thiazolidine-2,4-dione (T-174), edaglitazone (BM-13-1258), rivoglitazone (CS-011), and 5-(2,4-dioxothiazolidin-5-ylmethyl)-2-methoxy-N-(4-trifluoromethyl-benzyl)benzamide (KRP297).

Examples of non-glitazone type PPAR gamma agonists include, but are not limited to N-(2-benzoylphenyl)-L-tyrosine analogues, such as GI-262570, reglixane (JTT501) and FK-614 and metaglidasen (MBX-102).

Examples of dual PPAR gamma/PPAR alpha agonists include, but are not limited to omega.-[(oxoquinazolinylalkoxy)phenyl]alkanoates and analogs thereof including those described in PCT Publication No. WO 99/08501 and Diabetes 2000, 49(5), 759-767; tesaglitazar, muraglitazar and naveglitazar.

Examples of antidiabetic vanadium containing compounds include, but are not limited to those disclosed in the U.S. Pat. No. 5,866,563.

Metformin (dimethyldiguanide) and its hydrochloride salt is marketed under the trademark GLUCOPHAGE™.

Examples of insulin secretion enhancers include but are not limited to glucagon receptor antagonists (as described above), sulphonyl urea derivatives, incretin hormones or mimics thereof, especially glucagon-like peptide-1 (GLP-1) or GLP-1 agonists, beta-cell imidazoline receptor antagonists, and short-acting insulin secretagogues, like antidiabetic phenylacetic acid derivatives, antidiabetic D-phenylalanine derivatives, and mitiglinide and pharmaceutical acceptable salts thereof.

Examples of sulphonyl urea derivatives include, but are not limited to, glisoxepid, glyburide, glibenclamide, acetohexamide, chloropropamide, glibornuride, tolbutamide, tolazamide, glipizide, carbutamide, gliquidone, glyhexamide, phenbutamide, tolcyclamide; glimepiride and gliclazide. Tolbutamide, glibenclamide, gliclazide, glibornuride, gliquidone, glisoxepid and glimepiride can be administered in the form that they are marketed under the trademarks RASTINON HOECHST™, AZUGLUCON™, DIAMICRONT™, GLUBORID™, GLURENORM™, PRO-DIABAN™ and AMARYL™, respectively.

Examples of GLP-1 agonists include, but are not limited to those disclosed in U.S. Pat. Nos. 5,120,712, 5,118,666 and 5,512,549, and PCT Publication No. WO 91/11457. In particular, GLP-1 agonists include those compounds like GLP-1 (7-37) in which compound the carboxy-terminal amide functionality of Arg$^{36}$ is displaced with Gly at the 37$^{th}$ position of the GLP-1 (7-36)NH$_2$ molecule and variants and analogs thereof including GLN$^9$-GLP-1 (7-37), D-GLN$^9$-GLP-1 (7-37), acetyl LYS$^9$-GLP-1 (7-37), LYS$^{18}$-GLP-1 (7-37) and, in particular, GLP-1 (7-37)OH, VAL$^8$-GLP-1 (7-37), GLY$^8$-GLP-1 (7-37), THR$^8$-GLP-1 (7-37), GLP-1 (7-37) and 4-imidazopropionyl-GLP-1.

One particular example of a GLP-1 agonist is Extendatide, a 39-amino acid peptide amide, which is marketed under the trademark BYETTA™. Exenatide has the empirical formula $C_{184}H_{282}N_{50}O_{60}S$ and molecular weight of 4186.6 Daltons. The amino acid sequence for Exenatide is as follows: H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH$_2$ Examples of glucagon-like peptide-2 (GLP-2) or GLP-2 agonists include, but are not limited to those disclosed in U.S. Pat. No. 7,056,886 and PCT Publication Nos. WO 00/53208, WO 01/49314 and WO 03/099854. One particular example of a GLP-2 agonist is TEDUGLUTIDE™, a 39-amino acid peptide amide (NPS Pharmaceuticals, Inc.).

Examples of beta-cell imidazoline receptor antagonists include, but are not limited to those described in PCT Publication No. WO 00/78726 and J. Pharmacol. Exp. Ther. 1996; 278; 82-89.

An example of an antidiabetic phenylacetic acid derivative is repaglinide and pharmaceutically acceptable salts thereof.

Examples of antidiabetic D-phenylalanine derivatives include, but are not limited to nateglinide (N-[(trans4-isopropylcyclohexyl)-carbonyl]-D-phenylalanine, EP 196222 and EP 526171) and repaglinide ((S)-2-ethoxy-4-{2-[[3-methyl-1-1-[2-(1-piperidinyl)phenyl]butyl]-amino]-2-oxoethyl}benzoic acid, EP 0 147 850 A2 and EP 0 207 331 A1). Nateglinide is intended to include the particular crystal forms (polymorphs) disclosed in U.S. Pat. No. 5,488,510 and European Patent Publication No. EP 0526171 B1. Repaglinide and nateglinide may be administered in the form as they are marketed under the trademarks NOVONORM™ and STARLIX™, respectively.

Examples of alpha-Glucosidase inhibitors include, but are not limited to, acarbose, N-(1,3-dihydroxy-2-propyl)valiolamine (voglibose) and the 1-deoxynojirimycin derivative miglitol. Acarbose is 4",6"-dideoxy-4'-[(1S)-(1,4,6/5)-4,5,6-trihydroxy-3-hydroxymethyl-2-cyclo-hexenylamino)maltotriose. The structure of acarbose can as well be described as O-4,6-dideoxy-4-{[1S,4R,5S,6S]-4,5,6-trihydroxy-3-(hydroxymethyl)-2-cyclohexen-1-yl]-amino)-alpha-D-glucopyranosyl-(1-4)-O-alpha-D-glucopyranosyl-(1-4)-D-glucopyranose. (U.S. Pat. No. 4,062,950 and European Patent Publication No. EP 0 226 121). Acarbose and miglitol may be administered in the forms that they are marketed under the trademarks GLUCOBAY™ and DIASTABOL 50™ respectively.

Examples of inhibitors of gastric emptying other than GLP-1 include, but are not limited to those disclosed in J. Clin. Endocrinol. Metab. 2000, 85(3), 1043-1048, and Diabetes Care 1998; 21; 897-893, especially Amylin and analogs thereof such as pramlintide. Amylin is described in Diabetologia 39, 1996, 492-499.

Examples of $\alpha_2$-adrenergic antagonists include, but are not limited to midaglizole which is described in Diabetes 36, 1987, 216-220. The insulin that may be used in combination with Compound I include, but are not limited to animal insulin preparations extracted from the pancreas of bovine and pig; human insulin preparations genetically synthesized using *Escherichia coli* or yeast; zinc insulin; protamine zinc insulin; fragment or derivative of insulin (e.g., INS-1) and an oral insulin preparation.

In one particular embodiment, the antidiabetic compound administered in combination with Compound I is selected from the group consisting of nateglinide, mitiglinide, repaglinide, metformin, extendatide, rosiglitazone, tesaglitazar, pioglitazone, glisoxepid, glyburide, glibenclamide, acetohexamide, chloropropamide, glibornuride, tolbutamide, tolazamide, glipizide, carbutamide, gliquidone, glyhexamide, phenbutamide, tolcyclamide, glimepiride and gliclazide, including any pharmaceutically acceptable salts thereof.

Examples of the preparation and formulation of PTPase inhibitors, GSK-3 inhibitors, non-small molecule mimetic compounds, GFAT inhibitors, G6Pase inhibitors, glucagon receptor antagonists, PEPCK inhibitors, F-1,6-BPase inhibitors, GP inhibitors, RXR modulators, Beta-3 AR agonists, PDHK inhibitors, inhibitors of gastric emptying and UCP modulators are disclosed in the patents, applications and references provided herein.

In the case of combination therapy with Compound I, the other antidiabetic compound may be administered (e.g., route and dosage form) in a manner known per se for such compound. Compound I and the other antidiabetic compound may be administered sequentially (i.e., at separate times) or at the same time, either one after the other separately in two separate dose forms or in one combined, single dose form. In one particular embodiment, the other antidiabetic compound is administered with Compound I as a single, combined dosage form. The dose of the antidiabetic compound may be selected from the range known to be clinically employed for such compound. Any of therapeutic compounds of diabetic complications, antihyperlipemic compounds, antiobestic compounds or antihypertensive compounds can be used in combination with Compound I in the same manner as the above antidiabetic compounds. Examples of therapeutic compounds of diabetic complications include, but are not limited to, aldose reductase inhibitors such as tolrestat, epalrestat, zenarestat, zopolrestat, minalrestat, fidarestat, CT-112 and ranirestat; neurotrophic factors and increasing compounds thereof such as NGF, NT-3, BDNF and neurotrophin production-secretion promoters described in WO01/14372 (e.g., 4-(4-chlorophenyl)-2-(2-methyl-1-imidazolyl)-5-[3-(2-methylphenoxy)propyl]oxazole); neuranagenesis stimulators such as Y-128; PKC inhibitors such as ruboxistaurin mesylate; AGE inhibitors such as ALT946, pimagedine, N-phenacylthiazolium bromide (ALT766), ALT-711, EXO-226, pyridorin and pyridoxamine; reactive oxygen scavengers such as thioctic acid; cerebral vasodilators such as tiapride and mexiletine; somatostatin receptor agonists such as BIM23190; and apoptosis signal regulating kinase-1 (ASK-1) inhibitors. Examples of antihyperlipemic compounds include, but are not limited to, HMG-CoA reductase inhibitors such as pravastatin, simvastatin, lovastatin, atorvastatin, fluvastatin, rosuvastatin and pitavastatin; squalene synthase inhibitors such as compounds described in WO97/10224 (e.g., N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidine-4-acetic acid); fibrate compounds such as bezafibrate, clofibrate, simfibrate and clinofibrate; ACAT inhibitors such as avasimibe and eflucimibe; anion exchange resins such as colestyramine; probucol; nicotinic acid drugs such as nicomol and niceritrol; ethyl icosapentate; and plant sterols such as soysterol and γ-oryzanol. Examples of antiobestic compounds include, but are not limited to, dexfenfluramine, fenfluramine, phentermine, sibutramine, amfepramone, dexamphetamine, mazindol, phenylpropanolamine, clobenzorex; MCH receptor antagonists such as SB-568849 and SNAP-7941; neuropeptide Y antagonists such as CP-422935; cannabinoid receptor antagonists such as SR-141716 and SR-147778; ghrelin antagonist; 11β-hydroxysteroid dehydrogenase inhibitors such as BVT-3498; pancreatic lipase inhibitors such as orlistat and ATL-962; Beta-3 AR agonists such as AJ-9677; peptidic anorexiants such as leptin and CNTF (Ciliary Neurotropic Factor); cholecystokinin agonists such as lintitript and FPL-15849; and feeding deterrent such as P-57. Examples of the antihypertensive compounds include angiotensin converting enzyme inhibitors such as captopril, enalapril and delapril; angiotensin II antagonists such as candesartan cilexetil, losartan, eprosartan, valsartan, telmisartan, irbesartan, olmesartan medoxomil, tasosartan and 1-[[2'-(2, 5-dihydro-5-oxo-4H-1,2,4-oxadiazol-3-yl)biphenyl-4-yl] methyl]-2-ethoxy-1H-benzimidazole-7-carboxylic acid; calcium channel blockers such as manidipine, nifedipine, nicardipine, amlodipine and efonidipine; potassium channel openers such as levcromakalim, L-27152, AL0671 and NIP-121; clonidine; deacetylases such as reservatrol, sirtuin agonist, polyphenols; MCR4 agonist; Sodium dependent glucose transport (SGLT2) inhibitors.

The structure of the active agents identified herein by code nos., generic or trade names may be taken from the actual edition of the standard compendium "The Merck Index" or from databases, e.g. Patents International (e.g. IMS World Publications). The corresponding content thereof is hereby incorporated by reference. Any person skilled in the art is fully enabled to identify the active agents and, based on these references, likewise enabled to manufacture and test the pharmaceutical indications and properties in standard test models, both in vitro and in vivo.

4. Compositions Comprising Compound I

Compound I may be comprised within a pharmaceutical composition adapted for a variety of routes of administration. For example, Compound I may be comprised within a pharmaceutical composition adapted to be administered by a route selected from the group consisting of orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, intraperitoneally and intrathecally. As such, Compound I may be formulated in a variety of pharmaceutically acceptable compositions including injectable forms (e.g., subcutaneous, intravenous, intramuscular and intraperitoneal injections), drip infusions, external application forms (e.g., nasal spray preparations, transdermal preparations; ointments, etc.), and suppositories (e.g., rectal and vaginal suppositories). These different pharmaceutically acceptable compositions can be manufactured by known techniques conventionally used in the pharmaceutical industry with a pharmaceutically acceptable carrier conventionally used in the pharmaceutical industry.

As used herein, a composition comprising Compound I is intended to encompass the free base form of Compound I, salts, hydrates and prodrugs of Compound I, as well as other materials that may be included in such composition for its intended purpose, including other active ingredients, unless otherwise specified. Particular salt forms of Compound I that may be employed include, but are not limited to, the HCl, methanesulfonate, succinate, benzoate, toluenesulfonate, R-(−)mandelate or benzenesulfonate salt forms of Compound I.

As noted above, Compound I may advantageously be used when administered to a patient at a weekly dose of between 1 mg/week and 500 mg/week of Compound, optionally between 12.5 mg/week and 400 mg/week of Compound I, optionally between 20 mg/week and 400 mg/week, optionally between 20 mg/week and 200 mg/week of Compound I, optionally between 50 mg/week and 400 mg/week of Compound I, and optionally between 100 mg/week and 400 mg/week of Compound. Specific dosage amounts that may be used include, but are not limited to 3.125 mg, 12.5 mg, 20 mg, 25 mg, 50 mg, 75 mg, 100 mg, 125 mg, 150 mg, 175 mg, 200 mg 250 mg, 400 mg and 500 mg of Compound I per week. As also noted above, it is desirable for Compound I to be administered one time per week. Accordingly, pharmaceutical compositions of the present invention may be in the form of a single dose form comprising between 1 mg/week and 500 mg/week of Compound I, optionally between 12.5 mg/week and 400 mg/week of Compound I, optionally between 20 mg/week and 400 mg/week, optionally between 20 mg/week and 200 mg/week of Compound I, optionally between 50 mg/week and 400 mg/week of Compound I, and optionally between 100 mg/week and 400 mg/week of Compound I. In specific embodiments, the pharmaceutical composition comprises 3.125 mg, 12.5 mg, 20 mg, 25 mg, 50 mg, 75 mg, 100 mg, 125 mg, 150 mg, 175 mg, 200 mg 250 mg, 400 mg and 500 mg of Compound I. In each instance, the dosage amounts and ranges of Compound I provided is based on the molecular weight of the free base form of Compound I.

Compound I also may advantageously be used when administered to a patient at a weekly dose of more than 250 mg of Compound I, optionally at least 275 mg of Compound I, optionally at least 300 mg of Compound I, optionally at least 350 mg of Compound I, and optionally at least 400 mg of Compound I. In one variation, the weekly dose of Compound I administered to the patient is not more than 500 mg. In another variation, the weekly dose of Compound I administered to the patient is not more than 400 mg. In still another variation, the weekly dose of Compound I administered to the patient is not more than 350 mg. In yet another variation, the weekly dose of Compound I administered to the patient is more than 250 mg and not more than 500 mg. In a further variation, the weekly dose of Compound I administered to the patient is more than 250 mg and not more than 400 mg. Specific dosage amounts that may be used include, but are not limited to 275 mg, 300 mg, 350 mg, 400 mg or 500 mg of Compound I per week. In each instance, the dosage amounts and ranges of Compound I provided is based on the molecular weight of the free base form of Compound I.

As also noted above, it is desirable for Compound I to be administered one time per week. Accordingly, pharmaceutical compositions of the present invention may be in the form of a single dose form comprising a dose of between 1 mg/week and 500 mg/week of Compound I to a patient, optionally between 12.5 mg/week and 400 mg/week of Compound I, optionally between 20 mg/week and 400 mg/week, optionally between 20 mg/week and 200 mg/week of Compound I, optionally between 50 mg/week and 400 mg/week of Compound I, and optionally between 100 mg/week and 400 mg/week of Compound. In other variations, the pharmaceutical composition comprises 3.125 mg, 12.5 mg, 20 mg, 25 mg, 50 mg, 75 mg, 100 mg, 125 mg, 150 mg, 175 mg, 200 mg, 250 mg, 275 mg, 300 mg, 350 mg, 400 mg or 500 mg of Compound I. In each instance, the dosage amounts and ranges of Compound I provided is based on the molecular weight of the free base form of Compound I.

Pharmaceutical compositions of the present invention also may be in the form of a single dose form comprising a dose of more than 250 mg of Compound I, optionally at least 275 mg of Compound I, optionally at least 300 mg of Compound I, optionally at least 350 mg of Compound I, and optionally at least 400 mg of Compound I. In one variation, the pharmaceutical composition comprises not more than 500 mg of Compound I. In another variation, the pharmaceutical composition comprises not more than 400 mg of Compound I. In still another variation, the pharmaceutical composition comprises not more than 350 mg of Compound I. In yet another variation, the pharmaceutical composition comprises more than 250 mg and not more than 500 mg of Compound I. In a further variation, the pharmaceutical composition comprises more than 250 mg and not more than 400 mg of Compound I. In other variations, the pharmaceutical composition comprises 275 mg, 300 mg, 350 mg, 400 mg or 500 mg of Compound I. In each instance, the dosage amounts and ranges of Compound I provided is based on the molecular weight of the free base form of Compound I.

As also noted above, Compound I may advantageously be used when administered orally. Accordingly, the compositions of the present invention may optionally be adapted for oral administration. In one variation, such pharmaceutical composition is a solid formulation adapted for oral administration. In this regard, the composition, for example, may be in the form of a tablet or capsule. In another variation, such pharmaceutical composition is a liquid formulation adapted for oral administration.

As also noted above, Compound I may advantageously be used when administered parenterally. Accordingly, the compositions of the present invention may optionally be adapted for parenteral administration. In one variation, such pharmaceutical composition is a solution formulation adapted for parenteral administration. In another variation, such pharmaceutical composition is a suspension formulation adapted for parenteral administration.

As noted above, Compound I may advantageously be used in combination with one or more other antidiabetic and/or incretin compounds. Accordingly, the compositions of the present invention may optionally comprises Compound I in combination with one or more other antidiabetic or incretin compounds in a combined, single dose form. Optionally, such combined, single dose form comprising Compound I in combination with one or more other antidiabetic and/or incretin compounds is adapted for oral administration and optionally is a solid oral dose form. Alternatively, such combined, single dose form comprising Compound I in combination with one or more other antidiabetic and/or incretin compounds can be adapted for parenteral administration and optionally is a solution dose form.

In one variation, such combined, single dose form comprising Compound I in combination with one or more other antidiabetic compounds comprises a dose of between 1 mg/week and 500 mg/week of Compound I to a patient, optionally between 12.5 mg/week and 400 mg/week of Compound I, optionally between 20 mg/week and 400 mg/week, optionally between 20 mg/week and 200 mg/week of Compound I, optionally between 50 mg/week and 400 mg/week of Compound I, and optionally between 100 mg/week and 400 mg/week of Compound. In other variations, the pharmaceutical composition comprises 3.125 mg, 12.5 mg, 20 mg, 25 mg, 50 mg, 75 mg, 100 mg, 125 mg, 150 mg, 175 mg, 200 mg, 250 mg, 275 mg, 300 mg, 350 mg, 400 mg or 500 mg of Compound I.

In another variation, such combined, single dose form comprising Compound I in combination with one or more other antidiabetic compounds comprises a dose of more than 250 mg of Compound I, optionally at least 275 mg of Compound I, optionally at least 300 mg of Compound T, optionally at least 350 mg of Compound I, and optionally at least 400 mg of Compound I. In one variation, the pharmaceutical composition comprises not more than 500 mg of Compound I. In another variation, the pharmaceutical composition comprises not more than 400 mg of Compound I. In still another variation, the pharmaceutical composition comprises not more than 350 mg of Compound I. In yet another variation, the pharmaceutical composition comprises more than 250 mg and not more than 500 mg of Compound I. In a further variation, the pharmaceutical composition comprises more than 250 mg and not more than 400 mg of Compound I. In other variations, the pharmaceutical composition comprises 275 mg, 300 mg, 350 mg, 400 mg or 500 mg of Compound I.

Any antidiabetic compound, or set of antidiabetic compounds may be combined with Compound I to form such combined, single dose form. In particular embodiments, such combined, single dose form includes Compound I and one or more members of the group consisting of insulin signaling pathway modulators, like protein tyrosine phosphatase (PTPase) inhibitors, and glutamine-fructose-6-phosphate amidotransferase (GFAT) inhibitors, compounds influencing a dysregulated hepatic glucose production, like glucose-6-phosphatase (G6Pase) inhibitors, fructose-1,6-bisphosphatase (F-1,6-BPase) inhibitors, glycogen phosphorylase (GP) inhibitors, glucagon receptor antagonists and phosphoenolpyruvate carboxykinase (PEPCK) inhibitors, pyruvate dehydrogenase kinase (PDHK) inhibitors, insulin sensitivity enhancers (insulin sensitizers), insulin secretion enhancers (insulin secretagogues), alpha-glucosidase inhibitors, inhibitors of gastric emptying, glucokinase activators, GLP-1 receptor agonists, GLP-2 receptor agonists, UCP modulators, RXR modulators, GSK-3 inhibitors, PPAR modulators, metformin, insulin, and $\alpha_2$-adrenergic antagonists. Compound I may be administered with such at least one other antidiabetic compound either simultaneously as a single dose, at the same time as separate doses, or sequentially (i.e., where on is administered before or after the other is administered).

In one variation, such combined, single dose form comprises Compound I and an antidiabetic thiazolidinedione. Particular examples of thiazolidinediones that may be used in this variation include, but are not limited to (S)-((3,4-dihydro-2-(phenyl-methyl)-2H-1-benzopyran-6-yl)methyl-thiazolidine-2,4-dione (englitazone), 5-{[4-(3-(5-methyl-2-phenyl-4-oxazolyl)-1-oxo-propyl)-phenyl]-methyl}-thiazolidine-2, 4-dione (darglitazone), 5-{[4-(1-methyl-cyclohexyl) methoxy)-phenyl]methyl]-thiazolidine-2,4-dione (ciglitazone), 5-{[4-(2-(1-indolyl)ethoxy)phenyl]methyl}-thiazolidine-2,4-dione (DRF2189), 5-{4-[2-(5-methyl-2-phenyl-4-oxazoly)-ethoxy)]benzyl}-thiazolidine-2,4-dione (BM-13.1246), 5-(2-naphthylsulfonyl)-thiazolidine-2,4-dione (AY-31637), bis{4-[(2,4-dioxo-5-thiazolidinyl)-methyl] phenyl}methan-e (YM268), 5-{4-[2-(5-methyl-2-phenyl-4-oxazolyl)-2-hydroxyethoxy]-benzyl}-thiazolidine-2,4-dione (AD-5075), 5-[4-(1-phenyl-1-cyclopropanecarbonylamino)-benzyl]-thiazolidine-2,4-dione (DN-108) 5-{[4-(2-(2,3-dihydroindol-1-yl)ethoxy)phenylmethyl)-thiazolidine-2,4-dione, 5-[3-(4-chloro-phenyl])-2-propynyl]-5-phenylsulfonyl) thiazolidine-2,4-dione, 5-[3-(4-chlorophenyl])-2-propynyl]-5-(4-fluorophenyl-sulfonyl)thiazolidine-2,4-dione, 5-{[4-(2-(methyl-2-pyridinyl-amino)-ethoxy)phenyl]methyl}-thiazolidine-2,4-dione (rosiglitazone), 5-{[4-(2-(5-ethyl-2-pyridyl)ethoxy)phenyl]-methyl}-thiazolidine-2,4-dione (pioglitazone), 5-[6-(2-fluoro-benzyloxy)-naphthalen-2-yl-methyl]-thiazolidine-2,4-dione (MCC555), 5-([2-(2-naphthyl)-benzoxazol-5-yl]-methyl}thiazolidine-2,4-dione (T-174), edaglitazone (BM-13-1258), rivoglitazone (CS-011) and 5-(2,4-dioxothiazolidin-5-ylmethyl)-2-met-hoxy-N-(4-trifluoromethyl-benzyl)benzamide (KRP297).

In one particular variation, the thiazolidinedione in such combined, single dose form is 5-{[4-(2-(5-ethyl-2-pyridyl) ethoxy)phenyl]-methyl}-thiazolidine-2,4-dione (pioglitazone) and its hydrochloride salt which is marketed under the trademark ACTOS™.

In another particular variation, the thiazolidinedione is 5-{ [4-(2-(methyl-2-pyridinyl-amino)-ethoxy)phenyl]methyl}-thiazolidine-2,4-dione (rosiglitazone) and its maleate salt.

In another variation, such combined, single dose form comprises Compound I and a non-glitazone type PPAR gamma agonist.

In another variation, such combined, single dose form comprises Compound I and a biguanide. A particular example of a biguanide that may be used in this variation is Metformin (dimethyldiguanide) and its hydrochloride salt which is marketed under the trademark GLUCOPHAGE™.

In another variation, such combined, single dose form comprises Compound I and a sulphonyl urea derivative. Particular examples of sulphonyl urea derivatives that may be used in this variation include, but are not limited to glisoxepid, glyburide, glibenclamide, acetohexamide, chloropropamide, glibornuride, tolbutamide, tolazamide, glipizide, carbutamide, gliquidone, glyhexamide, phenbutamide, tolcyclamide; glimepiride and gliclazide. Tolbutamide, glibenclamide, gliclazide, glibornuride, gliquidone, glisoxepid and glimepiride can be administered in the form as they are marketed under the trademarks RASTINON HOECHST™, AZUGLUCON™, DIAMICRONT™, GLUBORID™, GLURENORM™, PRO-DIABAN™ and AMARYL™, respectively.

In another variation, such combined, single dose form comprises Compound I and an antidiabetic D-phenylalanine derivative. Particular examples of antidiabetic D-phenylalanine derivatives that may be used in this variation include, but are not limited to repaglinide and nateglinide which may be administered in the form as they are marketed under the trademarks NOVONORM™ and STARLIX™, respectively.

In another variation, such combined, single dose form comprises Compound I and an alpha-Glucosidase inhibitor. Particular examples of alpha-Glucosidase inhibitors that may be used in this variation include, but are not limited to acarbose, miglitol and voglibose which may be administered in the form as they are marketed under the trademarks GLUCOBAY™, DIASTABOL 50™ and BASEN™, respectively.

In one particular embodiment, the antidiabetic compound administered in combination with Compound I in such combined, single dose form is selected from the group consisting of nateglinide, repaglinide, metformin, extendatide, rosiglitazone, pioglitazone, glisoxepid, glyburide, glibenclamide, acetohexamide, chloropropamide, glibornuride, tolbutamide, tolazamide, glipizide, carbutamide, gliquidone, glyhexamide, phenbutamide, tolcyclamide, glimepiride and gliclazide, including any pharmaceutically acceptable salts thereof.

In regard to each of the above embodiments and variations regarding a combined, single dose form comprising the combination of Compound I and one or more other antidiabetic compounds, the pharmaceutical composition may optionally be adapted for oral administration and in this regard may optionally be a solid formulation such as a tablet or capsule or may alternatively be in a liquid formulation adapted for oral administration. The dose of the antidiabetic compound may be selected from the range known to be clinically employed for such compound. Any of therapeutic compounds of diabetic complications, antihyperlipemic compounds, antiobestic compounds or antihypertensive compounds can be used in combination with Compound I in the same manner as the above antidiabetic compounds. Examples of therapeutic compounds of diabetic complications include, but are not limited to, aldose reductase inhibitors such as tolrestat, epalrestat, zenarestat, zopolrestat, minalrestat, fidarestat, CT-112 and ranirestat; neurotrophic factors and increasing compounds thereof such as NGF, NT-3, BDNF and neurotrophin production-secretion promoters described in WO01/14372 (e.g., 4-(4-chlorophenyl)-2-(2-methyl-1-imidazolyl)-5-[3-(2-methylphenoxy)propyl]oxazole); neuranagenesis stimulators such as Y-128; PKC inhibitors such as ruboxistaurin mesylate; AGE inhibitors such as ALT946, pimagedine, N-phenacylthiazolium bromide (ALT766), ALT-711, EXO-226, pyridorin and pyridoxamine; reactive oxygen scavengers such as thioctic acid; cerebral vasodilators such as tiapride and mexiletine; somatostatin receptor agonists such as BIM23190; and apoptosis signal regulating kinase-1 (ASK-1) inhibitors. Examples of antihyperlipemic compounds include, but are not limited to, HMG-CoA reductase inhibitors such as pravastatin, simvastatin, lovastatin, atorvastatin, fluvastatin, rosuvastatin and pitavastatin; squalene synthase inhibitors such as compounds described in WO97/10224 (e.g., N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidine-4-acetic acid); fibrate compounds such as bezafibrate, clofibrate, simfibrate and clinofibrate; ACAT inhibitors such as avasimibe and eflucimibe; anion exchange resins such as colestyramine; probucol; nicotinic acid drugs such as nicomol and niceritrol; ethyl icosapentate; and plant sterols such as soysterol and γ-oryzanol. Examples of antiobestic compounds include, but are not limited to, dexfenfluramine, fenfluramine, phentermine, sibutramine, amfepramone, dexamphetamine, mazindol, phenylpropanolamine, clobenzorex; MCH receptor antagonists such as SB-568849 and SNAP-7941; neuropeptide Y antagonists such as CP-422935; cannabinoid receptor antagonists such as SR-141716 and SR-147778; ghrelin antagonist; 11β-hydroxysteroid dehydrogenase inhibitors such as BVT-3498; pancreatic lipase inhibitors such as orlistat and ATL-962; Beta-3 AR agonists such as AJ-9677; peptidic anorexiants such as leptin and CNTF (Ciliary Neurotropic Factor); cholecystokinin agonists such as lintitript and FPL-15849; and feeding deterrent such as P-57. Examples of the antihypertensive compounds include angiotensin converting enzyme inhibitors such as captopril, enalapril and delapril; angiotensin II antagonists such as candesartan cilexetil, losartan, eprosartan, valsartan, telmisartan, irbesartan, olmesartan medoxomil, tasosartan and 1-[[2'-(2,5-dihydro-5-oxo-4H-1,2,4-oxadiazol-3-yl)biphenyl-4-yl]methyl]-2-ethoxy-1H-benzimidazole-7-carboxylic acid; calcium channel blockers such as manidipine, nifedipine, nicardipine, amlodipine and efonidipine; potassium channel openers such as levcromakalim, L-27152, AL0671 and NIP-121; and clonidine.

5. Kits and Articles of Manufacture Comprising Compound I

The present invention also relates to kits comprising a pharmaceutical composition according to the present invention comprising Compound I (and optionally one or more other antidiabetic or incretin compounds) where such kit further comprises instructions that include one or more forms of information selected from the group consisting of indicating a disease state for which the pharmaceutical composition is to be administered, storage information for the pharmaceutical composition, dosing information and instructions regarding how to administer the pharmaceutical composition. The kit may also comprise packaging materials. The packaging material may also comprise a container for housing the pharmaceutical composition. The container may optionally comprise a label indicating the disease state for which the pharmaceutical composition is to be administered, storage information, dosing information and/or instructions regarding how to administer the composition. The kit may also comprise additional components for storage or administration of the composition. The kit may also comprise the composition in single or multiple dose forms.

In one embodiment, the pharmaceutical composition in the kit comprises multiple doses of a pharmaceutical composition according to the present invention wherein such pharmaceutical composition is a single dose form that comprises Compound I in one of the dosage ranges specified herein.

In another embodiment, the pharmaceutical composition in the kit comprises multiple doses of a pharmaceutical composition according to the present invention wherein such pharmaceutical composition is a single dose form that comprises Compound I and one or more of the other antidiabetic or incretin compounds specified herein.

The present invention also relates to articles of manufacture comprising a pharmaceutical composition according to the present invention comprising Compound I (and optionally one or more other antidiabetic or incretin compounds) where such articles of manufacture further comprise packaging materials. In one variation, the packaging material comprises a container for housing the composition. In another variation, the invention provides an article of manufacture where the container comprises a label indicating one or more members of the group consisting of a disease state for which the composition is to be administered, storage information, dosing information and/or instructions regarding how to administer the composition.

In one embodiment, the pharmaceutical composition in the article of manufacture comprises multiple doses of a pharmaceutical composition according to the present invention wherein such pharmaceutical composition is a single dose form that comprises Compound I in one of the dosage ranges specified herein.

In another embodiment, the pharmaceutical composition in the article of manufacture comprises multiple doses of a pharmaceutical composition according to the present invention wherein such pharmaceutical composition is a single dose form that comprises Compound I and one or more of the other antidiabetic or incretin compounds specified herein.

It is noted that the packaging material used in kits and articles of manufacture according to the present invention may form a plurality of divided containers such as a divided bottle or a divided foil packet. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container that is employed will depend on the exact dosage form involved. It is feasible that more than one container can be used together in a single package to market a single dosage form. For example, tablets may be contained in a bottle that is in turn contained within a box.

One particular example of a kit according to the present invention is a so-called blister pack. Blister packs are well known in the packaging industry and are being widely used for the packaging of pharmaceutical unit dosage forms (tablets, capsules, and the like). Blister packs generally consist of a sheet of relatively stiff material (preferably stiff transparent plastic material) covered with a foil. During the packaging process recesses are formed in the stiff material. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the foil and the sheet. The strength of the sheet is preferably such that the tablets or capsules can be removed from the blister pack by manually applying pressure on the recesses whereby an opening is formed in the foil at the place of the recess. The tablet or capsule can then be removed via said opening.

EXAMPLES

1. Preparation of 2-[6-(3-Amino-piperidin-1-yl)-3-methyl-2,4-dioxo-3,4-dihydro-2H-pyrimidin-1-ylm-ethyl]-4-fluoro-benzonitrile and Pharmaceutically Acceptable Salts

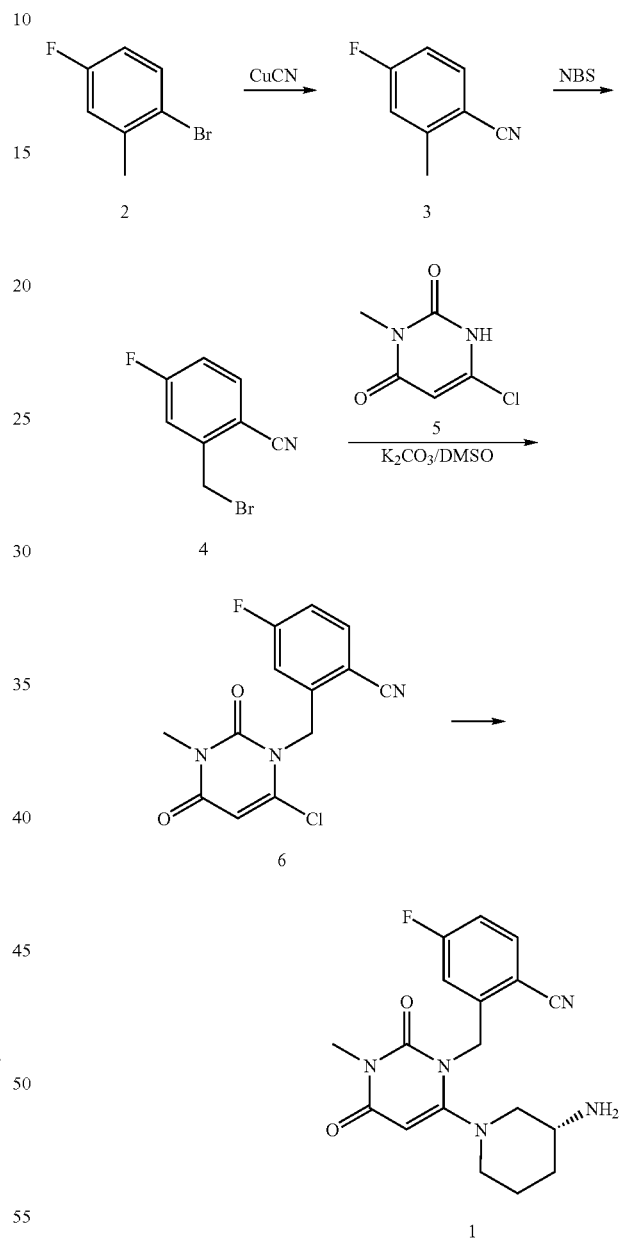

4-Fluoro-2-methylbenzonitrile (3)

A mixture of 2-bromo-5-fluorotoluene (2) (3.5 g, 18.5 mmol) and CuCN (2 g, 22 mmol) in DMF (100 mL) was refluxed for 24 hours. The reaction was diluted with water and extracted with hexane. The organics were dried over MgSO$_4$ and the solvent removed to give product 3 (yield 60%). $^1$H-NMR (400 MHz, CDCl$_3$): δ 7.60 (dd, J=5.6, 8.8 Hz, 1H), 6.93-7.06 (m, 2H), 2.55 (s, 3H).

2-Bromomethyl-4-fluorobenzonitrile (4)

A mixture of 4-fluoro-2-methylbenzonitrile (3) (2 g, 14.8 mmol), NBS (2.64 g, 15 mmol) and AIBN (100 mg) in $CCl_4$ was refluxed under nitrogen for 2 hours. The reaction was cooled to room temperature. The solid was removed by filtration. The organic solution was concentrated to give crude product as an oil, which was used in the next step without further purification. $^1$H-NMR (400 MHz, $CDCl_3$): δ 7.68 (dd, J=5.2, 8.4 Hz, 1H), 7.28 (dd, J=2.4, 8.8 Hz, 1H), 7.12 (m, 1H), 4.6 (s, 2H).

2-(6-Chloro-3-methyl-2,4-dioxo-3,4-dihydro-2H-pyrimidin-1-ylmethyl)-4-fluoro-benzonitrile (6)

A mixture of crude 3-methyl-6-chlorouracil (5) (0.6 g, 3.8 mmol), 2-Bromomethyl-4-fluorobenzonitrile (0.86 g, 4 mmol) and $K_2CO_3$ (0.5 g, 4 mmol) in DMSO (10 mL) was stirred at 60° C. for 2 hours. The reaction was diluted with water and extracted with EtOAc. The organics were dried over $MgSO_4$ and the solvent removed. The residue was purified by column chromatography. 0.66 g of the product was obtained (yield: 60%). $^1$H-NMR (400 MHz, $CDCl_3$): δ 7.73 (dd, J=7.2, 8.4 Hz, 1H), 7.26 (d, J=4.0 Hz, 1H), 7.11-7.17 (m, 1H), 6.94 (dd, J=2.0, 9.0 Hz, 1H), 6.034 (s, 2H), 3.39 (s, 3H). MS (ES) [m+H] calc'd for $C_{13}H_9ClFN_3O_2$, 293.68; found 293.68.

2-[6-(3-Amino-piperidin-1-yl)-3-methyl-2,4-dioxo-3,4-dihydro-2H-pyrimidin-1-ylmethyl]-4-fluoro-benzonitrile, TFA Salt (1) (TFA salt of Compound I)

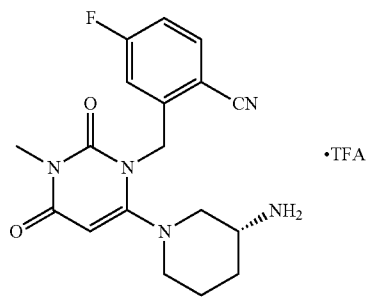

2-(6-Chloro-3-methyl-2,4-dioxo-3,4-dihydro-2H-pyrimidin-1-ylmethyl)-4-fluoro-benzonitrile (5) (300 mg, 1.0 mmol), (R)-3-amino-piperidine dihydrochloride (266 mg, 1.5 mmol) and sodium bicarbonate (500 mg, 5.4 mmol) were stirred in a sealed tube in EtOH (3 mL) at 100° C. for 2 hrs. The final compound was obtained as a TFA salt after HPLC purification. $^1$H-NMR (400 MHz, $CD_3OD$): δ. 7.77-7.84 (m, 1H), 7.16-7.27 (m, 2H), 5.46 (s, 1H), 5.17-5.34 (ABq, 2H, J=35.2, 15.6 Hz), 3.33-3.47 (m, 2H), 3.22 (s, 3H), 2.98-3.08 (m, 1H), 2.67-2.92 (m, 2H), 2.07-2.17 (m, 1H), 1.82-1.92 (m, 1H), 1.51-1.79 (m, 2H). MS (ES) [m+H] calc'd for $C_{18}H_{20}FN_5O_2$, 357.38; found, 357.38.

2-[6-(3-Amino-piperidin-1-yl)-3-methyl-2,4-dioxo-3,4-dihydro-2H-pyrimidin-1-ylmethyl]-4-fluoro-benzonitrile, HCl Salt

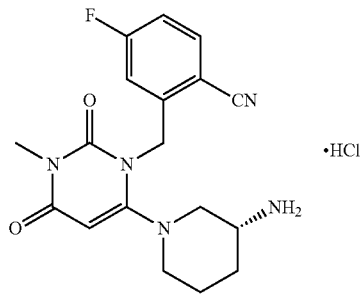

The TFA salt of Compound I was suspended in DCM, and then washed with saturated $Na_2CO_3$. The organic layer was dried and removed in vacuo. The residue was dissolved in acetonitrile and HCl in dioxane (1.5 eq.) was added at 0° C. The HCl salt was obtained after removing the solvent. $^1$H-NMR (400 MHz, $CD_3OD$): δ. 7.77-7.84 (m, 1H), 7.12-7.26 (m, 2H), 5.47 (s, 1H), 5.21-5.32 (ABq, 2H, J=32.0, 16.0 Hz), 3.35-3.5 (m, 2H), 3.22 (s, 3H), 3.01-3.1 (m, 1H), 2.69-2.93 (m, 2H), 2.07-2.17 (m, 1H), 1.83-1.93 (m, 1H), 1.55-1.80 (m, 2H). MS (ES) [m+H] calc'd for $C_{18}H_{20}FN_5O_2$, 357.38; found, 357.38.

General Procedure for the Preparation of Salts of Compound I

The benzonitrile product may be isolated as the free base if desired, but preferably, the product may be further converted to a corresponding acid addition salt. Specifically, the benzonitrile product (approximately 10 mg) in a solution of MeOH (1 mL) was treated with various acids (1.05 equivalents). The solutions were allowed to stand for three days open to the air. If a precipitate formed, the mixture was filtered and the salt dried. If no solid formed, the mixture was concentrated in vacuo and the residue isolated. In this way, salts of Compound I were prepared from the following acids: benzoic, p-toluenesulfonic, succinic, R-(−)-Mandelic and benzenesulfonic.

The isolation and/or purification steps of the intermediate compounds in the above described process may optionally be avoided if the intermediates from the reaction mixture are obtained as relatively pure compounds and the by-products or impurities of the reaction mixture do not interfere with the subsequent reaction steps. Where feasible, one or more isolation steps may be eliminated to provide shorter processing times, and the elimination of further processing may also afford higher overall reaction yields.

2. Effect of Administration on Plasma DPP-IV Activity

A single dose of Compound I was administered orally to 6 humans at a dosage of 12.5 mg, 25 mg, 50 mg, 100 mg, 200 mg and 400 mg, respectively (total 36 humans). FIG. 1 illustrates the observed effect that administering Compound I has on the human plasma DPP-IV activity post dosing. As can be seen, Compound I reduced DPP-IV activity in human plasma by greater than 10% relative to baseline at 168 hours post dosing. Thus, as can be seen from the data shown in FIG. 1, by administering Compound I one time per week at the dosage levels specified herein, Compound I can be effectively used relative to disease states where it is desired to reduce plasma DPP-IV activity. In view of the data presented, it is believed that when at least 50 mg of Compound I is administered to a patient, the patient's plasma DPP-IV activity may be reduced by greater than 35% relative to baseline for a period of at least 168 hours following administration, when at least 100 mg of Compound I is administered to a patient, the patient's plasma DPP-IV activity may be reduced by greater than 60% relative to baseline for a period of at least 168 hours following administration, and, when at least 200 mg of Compound I is administered to a patient, the patient's plasma DPP-IV activity may be reduced by greater than 70% relative to baseline for a period of at least 168 hours following administration.

3. Effect of Administration on Plasma DPP-IV Activity

A single dose of Compound I was administered orally to humans at a dosage of 3.125 mg (to 9 humans), 12.5 mg (to 8 humans), 50 mg (to 7 humans) and 100 mg (to 8 human), respectively. FIG. 2 illustrates the observed effect that administering Compound I has on the human plasma DPP-IV activity post dosing. As can be seen, Compound I reduced DPP-IV activity in human plasma by greater than 20% relative to baseline at 168 hours post dosing. Thus, as can be seen from the data shown in FIG. 2, by administering Compound I one time per week at the dosage levels specified herein, Compound I can be effectively used relative to disease states where it is desired to reduce plasma DPP-IV activity. In view of the data presented, it is believed that when at least 50 mg of Compound I is administered to a patient, the patient's plasma DPP-IV activity may be reduced by greater than 65% relative to baseline for a period of at least 168 hours following administration.

It will be apparent to those skilled in the art that various modifications and variations can be made to the compounds, compositions, kits, and methods of the present invention without departing from the spirit or scope of the invention. Thus, it is intended that the present invention cover the modifications and variations of this invention provided they come within the scope of the appended claims and their equivalents.

What is claimed is:

1. A pharmaceutical composition formulated in a single weekly dose form comprising more than 250 mg of Compound I having the formula

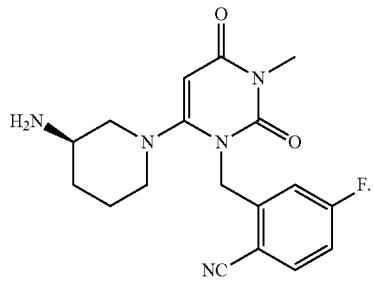

2. The pharmaceutical composition according to claim 1, wherein the single weekly dose form comprises at least 275 mg of Compound I.

3. The pharmaceutical composition according to claim 1, wherein the single weekly dose form comprises at least 300 mg of Compound I.

4. The pharmaceutical composition according to claim 1, wherein the single weekly dose form comprises at least 350 mg of Compound I.

5. The pharmaceutical composition according to claim 1, wherein the single weekly dose form comprises not more than 500 mg of Compound I.

6. The pharmaceutical composition according to claim 1, wherein the single weekly dose form comprises not more than 400 mg of Compound I.

7. The pharmaceutical composition according to claim 1, wherein the single weekly dose form comprises not more than 350 mg of Compound I.

8. The pharmaceutical composition according to claim 1, wherein the single weekly dose form comprises more than 250 mg and not more than 500 mg of Compound I.

9. The pharmaceutical composition according to claim 1, wherein the single weekly dose form comprises more than 250 mg and not more than 400 mg of Compound I.

10. The pharmaceutical composition according to claim 1, wherein Compound I is present in the pharmaceutical composition as a free base.

11. The pharmaceutical composition according to claim 1, wherein Compound I is present in the pharmaceutical composition in a pharmaceutically acceptable salt.

12. The pharmaceutical composition according to claim 1, wherein Compound I is present in the pharmaceutical composition in a succinate salt.

* * * * *